United States Patent
Chung et al.

(10) Patent No.: US 11,167,037 B2
(45) Date of Patent: Nov. 9, 2021

(54) ANTIBODY DRUG CONJUGATE PLATFORM USING BISPECIFIC ANTIBODY

(71) Applicant: SEOUL NATIONAL UNIVERSITY R&DB FOUNDATION, Seoul (KR)

(72) Inventors: Junho Chung, Gyeonggi-Do (KR); Junyeong Jin, Gyeonggi-do (KR); Hyori Kim, Seoul (KR); Gunwoo Park, Gyeonggi-do (KR); Soohyun Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 389 days.

(21) Appl. No.: 16/309,577

(22) PCT Filed: Jun. 21, 2017

(86) PCT No.: PCT/KR2017/006552
§ 371 (c)(1),
(2) Date: Dec. 13, 2018

(87) PCT Pub. No.: WO2017/222310
PCT Pub. Date: Dec. 28, 2017

(65) Prior Publication Data
US 2019/0328894 A1    Oct. 31, 2019

Related U.S. Application Data

(60) Provisional application No. 62/352,804, filed on Jun. 21, 2016.

(51) Int. Cl.
| | |
|---|---|
| A61K 47/68 | (2017.01) |
| A61K 47/65 | (2017.01) |
| A61P 35/00 | (2006.01) |
| A61K 31/407 | (2006.01) |
| A61K 31/4188 | (2006.01) |
| C07K 16/28 | (2006.01) |
| C07K 16/46 | (2006.01) |
| A61K 39/00 | (2006.01) |

(52) U.S. Cl.
CPC ........ *A61K 47/6803* (2017.08); *A61K 31/407* (2013.01); *A61K 31/4188* (2013.01); *A61K 47/65* (2017.08); *A61K 47/6849* (2017.08); *A61K 47/6879* (2017.08); *A61P 35/00* (2018.01); *C07K 16/2863* (2013.01); *C07K 16/468* (2013.01); *A61K 2039/505* (2013.01); *C07K 2317/24* (2013.01); *C07K 2317/31* (2013.01); *C07K 2317/526* (2013.01); *C07K 2317/56* (2013.01); *C07K 2317/94* (2013.01)

(58) Field of Classification Search
CPC .......... A61K 2039/505; A61K 47/6803; A61K 47/6849; A61K 31/407; A61K 47/65; A61K 47/6879; A61K 31/4188; C07K 16/2863; C07K 2317/56; C07K 2317/526; C07K 16/468; C07K 2317/24; C07K 2317/31; C07K 2317/94; A61P 35/00
See application file for complete search history.

(56) References Cited

U.S. PATENT DOCUMENTS

2008/0226650 A1    9/2008 Park et al.

FOREIGN PATENT DOCUMENTS

WO    WO-2012/141554 A2    10/2012

OTHER PUBLICATIONS

Kim et al., Bispecific anti-mPDGFRβ x cotinine scFv-Ck-scFv fusion protein and cotinine-duocarmycin can form antibody-drug conjugate-like complexes that exert cytotoxicity against mPDGFRβ expressing cells. Methods 154: 125-135, 2019.*
Jin et al., An anti-EGFR x cotinine bispecific antibody complexed with cotinine-conjugated duocarmycin inhibits growth of GFR-positive cancer cells with KRAS mutations. Experimental & Molecular Medicine 50:67, pp. 1-14, 2018.*
International Search Report from corresponding PCT Application No. PCT/KR2017/006552, dated Sep. 29, 2017.
Yoon, S., et al.; "Bispecific Her2 x cotinine antibody in combination with cotinine-(histidine)2-iodine for the pre?targeting of Her2? positive breast cancer xenografts", J Cancer Res Clin Oncol (2014) 140:227-233.
Kim, H., et al.; "In vitro and in vivo application of anti-cotinine antibody and cotinine-conjugated compounds" BMB Rep. 2014; 47(3): 130-134.
Kim, H., et al.; "Application of bispecific antibody against antigen and hapten for immunodetection and immunopurification", Experimental & Molecular Medicine (2013) 45, e43.

* cited by examiner

Primary Examiner — Ruixiang Li
(74) Attorney, Agent, or Firm — Harness, Dickey & Pierce, P.L.C.

(57) ABSTRACT

The present invention relates to an antibody drug conjugate using a bispecific antibody and its use. The antibody drug conjugate of the present invention can easily form a conjugate of an antibody and a drug without a multistep synthetic process though binding of a conjugate of a bivalent cotinine-peptide and a drug, and an anti-cotinine single chain variable fragment. In addition, the antibody drug conjugate can effectively deliver a drug to a target to which the antibody binds specifically, and can enhance a half-life of a drug in the body, thereby improving a therapeutic effect.

13 Claims, 16 Drawing Sheets
Specification includes a Sequence Listing.

ANTIBODY DRUG CONJUGATE PLATFORM USING BISPECIFIC ANTIBODY

CROSS-REFERENCE TO RELATED APPLICATIONS

This application is a national phase application of PCT Application No. PCT/KR2017/006552, filed on Jun. 21, 2017, which claims priority to U.S. Patent Application No. 62/352,804, filed on Jun. 21, 2016. The entire disclosures of the applications identified in this paragraph are incorporated herein by references.

FIELD

The present invention relates to an antibody drug conjugate using a bispecific antibody and its use.

BACKGROUND

An antibody drug conjugate (ADC) is a new category of anti-cancer agents and is developed to selectively deliver a cytotoxic agent to an antigen-expressing tumor cell. The conventional ADC has many advantages of high applicability and using a site-specific binding method. However, to link the cytotoxic agent to the antibody, a multistep binding method is required, and a process of optimizing individual antibodies is needed, and therefore there is a difficulty in use of ADC.

Epidermal growth factor receptor (EGFR) is a receptor tyrosine kinase that belongs to the ErbB family. Over-expression of EGFR is frequently observed in various human cancers, including head and neck cancer, colorectal cancer, lung cancer, breast cancer, prostate cancer, kidney cancer, pancreatic cancer, ovarian cancer, brain cancer and bladder cancer. Two pharmacological approaches have been used to block EGFR signals in the cancer treatment: monoclonal antibodies, cetuximab (Erbitux) and panitumumab (Vetibix) and small-molecule tyrosine kinase inhibitors, gefitinib (Iressa) and erlotinib (Tarceva). However, some mutations in EGFR and its downstream signaling molecules have led to a poor clinical response and difficulties in EGFR-targeted therapy. For example, KRAS mutations have an effect on primary resistance in EGFR targeted therapy among EGFR positive cancer patients. The KRS mutations are found in 25% of non-small cell lung cancer (NSCLC) and 39% of colorectal cancer cases. Although it has been well established that KRAS is one of the commonly occurring oncogene aberrations in human cancer, effective treatment is not available yet.

On the other hand, ADC may be effective on EGFR positive cancer having KRAS mutation. The ADC can be prepared by cross-linking a cytotoxic agent to a monoclonal antibody by a linker. The ADC can overcome the therapeutic limitation of the conventional antibody or non-specific cytotoxic agent. For example, two ADCs, brentuximab vedotin (Adcetris) and trastuzumab emtansine (Kadcyla) were approved by Food and Drug Administration (FDA) for the treatment of lymphoma and human epidermoid growth factor receptor-2 (Her2)-positive metastatic breast cancer, respectively.

Traditional conjugation of a small-molecule to an antibody uses ε-amino acid chains of lysine residues or deoxidized inter-chain disulfide bond on cysteine residues. Non-specific conjugations produce heterogeneous mixture of ADCs with variable drug to antibody ratios (DARs) and location of conjugation site. Such heterogeneity can have an impact on solubility, stability, pharmacokinetics and batch variation on ADCs.

To avoid the heterogeneity of ADCs as above, a site-specific conjugation method using intentional insertion of cysteine residue or unnatural amino acid residue, or enzymatic conjugation has been researched. In addition, binding activity, stability and conjugation efficiency of ADCs varies with different conjugation site. Hence, to maximize the properties of ADCs, a process of finding a proper conjugation residue and optimizing it to each antibody is required. Commonly, the ADCs requires multistep-complex conjugation process and sophisticated analysis for validation of the final product. As a result, there has been a lot of difficulties to develop the conventional ADCs using site-specific conjugation.

SUMMARY

Technical Problem

A problem to be solved of the present invention is to provide a new antibody drug conjugate platform in which a disadvantage that the conventional antibody drug conjugate has is resolved.

In addition, a problem to be solved of the present invention is to provide a pharmaceutical composition comprising the antibody drug conjugate platform and a method for treating a disease using it.

Technical Solution

The present invention provides an antibody drug conjugate platform comprising a bispecific antibody comprising an anti-cotinine single chain variable fragment (scFv); and a conjugate of bivalent cotinine which is cross-linked with a peptide, and a drug.

The inventors of the present invention have intensively studied to solve the disadvantage that the conventional antibody drug conjugates (ADC) require a multi-step binding procedure and optimization of the antibody, and as a result, they developed a new antibody drug conjugate platform using a tetravalent bispecific antibody that simultaneously binds to both human EGFR and hapten-conjugated cytotoxic agents.

First, the present inventors selected the previously reported tetravalent bispecific antibody format, and developed a bispecific antibody that reacts to human EGFR and cotinine. The bispecific antibody of the present invention uses an anti-cotinine single chain variable fragment (scFv) for complex formation with cotinine. Cotinine is the major metabolite of nicotine, which can be used as an ideal hapten in clinical approaches due to exogenous, physiological inertness and non-toxicity.

In one example of the present invention, the bispecific antibody (ERC6) of the present invention is formed as comprising the human EGFR binding antibody, cetuximab. Then, duocarmycin prepared the cross-linked bivalent cotinine binding peptide (cotinine-duocarmycin) and the antibody drug conjugate was formed by mixing with the bispecific antibody. As a result, the inventors of the present invention developed an antibody drug conjugate platform consisting of tetravalent conjugate comprising bispecific cetuximab×anti-cotinine antibody and bivalent cotinine binding peptide cross-linked with duocarmycin (cotinine-duocarmycin) (FIG. 1a). The antibody drug conjugate platform of the present invention showed the significant anti-tumor activity to EGFR-positive cetuximab refractory lung adenocarcinoma having a KRAS mutation in both in vitro and in vivo models. This experimental result indicates that the ADC platform of the present invention using the bispecific antibody can be a useful delivery tool for treatment of diseases such as cancer.

The anti-cotinine single chain variable fragment (scFv) of the bispecific antibody of the present invention can form an antibody drug conjugate by specifically binding to the bivalent cotinine of the drug-conjugated bivalent cotinine-peptide. The nucleotide sequence of the anti-cotinine single chain variable fragment can consist of the heavy chain of SEQ ID NO: 1 and the light chain of SEQ ID NO: 2. In addition, the amino acid sequence of the anti-cotinine single chain variable fragment can consist of the heavy chain of SEQ ID NO: 3 and the light chain of SEQ ID NO: 4. Moreover, the amino acid sequence (Gly-Gly-Gly-Gly-Ser)$_n$ ((SEQ ID NO: 11) where n is a whole number of 1~5), preferably (Gly-Gly-Gly-Gly-Ser)$_4$ (SEQ ID NO: 12) can be inserted between the heavy chain and light chain sequences of the anti-cotinine single chain variable fragment. Through this, it can help expressed anti-cotinine single chain variable fragment to perform an antigen-antibody reaction appropriately.

Preferably, the bispecific antibody of the present invention can insert the glycine and serine-rich peptide linker (Gly-Gly-Gly-Gly-Ser)$_n$ ((SEQ ID NO: 11) where n is a whole number of 1~5), preferably (Gly-Gly-Gly-Gly-Ser)$_3$ (SEQ ID NO: 13) between the $C_H3$ domain and anti-cotinine single chain variable fragment (scFv). Through this, the bispecific antibody of the present invention can improve flexibility.

Herein, the bivalent cotinine may be that two cotinines are cross-linked to the N terminal and C-terminal of a 6~18 mer peptide, respectively. Preferably, when the cotinine and peptide are conjugated, the cotinine may be carboxycotinine (trans-4-cotinine carboxylic acid), and cross-linking with the peptide can be effectively achieved through its carboxylic group.

Herein, the, as the peptide cross-linked with two cotinines, a 6~18 mer length of peptide may be used. The peptide may consist of one or more selected from the group consisting of glycine (G), serine (S) and lysine (K), etc. Preferably, as the peptide, GSKGSK (SEQ ID NO: 14), GGGGSKGGGGSK (SEQ ID NO: 15), GSKGSKGSKG-SKK (SEQ ID NO: 16), or GGGSGGGSKGGGSGGGSK (SEQ ID NO: 17), etc. may be used. More preferably, as the peptide, GSKGSKGSKGSKK (SEQ ID NO: 18) may be used, and this may be stably conjugated with the drug of the present invention, for example, duocarmycin.

Herein, conjugation of the bivalent cotinine and drug may be achieved through conjugation of an epsilon amino group of a lysine residue in a 6~18 mer peptide cross-linked with the bivalent cotinine and the drug.

The drug used for the antibody drug conjugate of the present invention may be any one selected from the group consisting of duocarmycin, auristatin, colchicine, anthracycline, calicheamicin, maytansinoid, pyrrolobenzodiazepine, dolastatin, tubulysin, maytansinoid, doxorubicin, cryptophycin, epothilone, safranin, deacetyl colchicine, maytansinol, vedotin, mafodotin, emtansine, mertansine, ravtansine, soravtansine, talirine, tesirine, indolinobenzodiazepines, irinotecan prodrug, exatecan derivative and tubulin inhibitor, etc., which are cytotoxic agents. Preferably, the antibody drug conjugate of the present invention may comprise duocarmycin or emtansine. The duocarmycin may be used as an effective cytotoxic drug for killing cancer cells due to strong DNA alkylation activity. For example, when duocarmycin forms a drug conjugate by combining with a peptide, it may be used in a form of 4 of valine-citrulline PAB-linked dimethyl aminoethyl duocarmycins. In addition, for example, when emtansine forms a drug conjugate by combining with a peptide, it can be combined through an MCC (maleimidomethyl cyclohexane-1-carboxylate) linker. In the experimental examples of the present invention, the cytotoxicity of the antibody-drug conjugate comprising duocarmycin (FIG. 3e) or emtansine (FIG. 6b) to cancer cells was experimented, and in both cases, the significant inhibitory activity to A549 cells was shown. From this result, it can be seen that the antibody drug conjugate platform of the present invention has versatility to be combined with the above various drugs.

In addition, the drug used for the antibody drug conjugate of the present invention may be siRNA inhibiting expression of a gene occurring cancer. For example, the siRNA may be selected from siRNA inhibiting the expression of one or more genes selected from the group consisting of Mcl-1, Wnt-1, Hec1, Survivin, Livin, Bcl-2, XIAP, Mdm2, EGF, EGFR, VEGF, VEGFR, GASC1, IGF1R, Akt1, Grp78, STAT3, STAT5a, β-catenin, WISP1, c-myc, RRM2, KSP, PKN3, PLK1, KRAS, MYC and EPHA2, etc. Herein, the siRNA inhibits the expression of specific gene that is expressed in cancer cells by ribonucleic acid-mediated interference (RNA-mediated interference, RNAi) to kill cancer cells, and therefore, the antibody drug conjugate comprising it can be used as an excellent anti-cancer agent.

Herein, conjugation of the siRNA and cotinine-peptide may be achieved through a linker. Through this, the antibody-drug conjugate of the present invention has versatility to bind various kinds of siRNA to the conjugate. For example, the linker may be SMCC (succinimidyl trans-4-(maleimidylmethyl)cyclohexane-1-carboxylate) linker or valine-citrulline-PAB linker. Specifically, when siRNA is combined to the cotinine-peptide through the SMCC linker, the 5' or 3' end of the siRNA may be modified and cross-linked to the SMCC linker, and it may be conjugated to cotinine-GSCGSCGSCGSCK-cotinine (C=cysteine). Otherwise, when siRNA is combined to the cotinine-peptide through the valine-citrulline-PAB linker, the siRNA may be conjugated to cotinine-GSKGSKGSKGSKK-cotinine through the linker.

The bispecific antibody comprised in the antibody drug conjugate of the present invention may comprise any one selected from the group consisting of cetuximab, trastuzumab, oregovomab, edrecolomab, alemtuzumab, labetuzumab, bevacizumab, ibritumomab, ofatumumab, panitumumab, rituximab, tositumomab, ipilimumab, gemtuzumab, brentuximab, vadastuximab, glembatumumab, depatuxizumab, polatuzumab, denintuzumab, enfortumab, telisotuzumab, tisotumab, pinatuzumab, lifastuzumab, indusatumab, vandortuzumab, sofituzumab, vorsetuzumab, trastuzumab, mirvetuximab, coltuximab, naratuximab, indatuximab, anetumab, lorvotuzumab, cantuzumab, lapritaximab, bivatuzumab, vadastuximab, rovalpituzumab, inotuzumab, sacituzumab, labetuzumab, milatuzumab, lupartumab and aprutumab, etc. Preferably, the antibody drug conjugate of the present invention may comprise the human EGFR binding antibody, cetuximab. Cetuximab is a monoclonal antibody clinically approved by FDA for treatment of non-small cell carcinoma, metastatic colon cancer, or head and neck squamous cell carcinoma (HN-SCC). The nucleotide sequence of cetuximab may consist of the heavy chain of SEQ ID NO: 5 and the light chain of SEQ ID NO: 6. In addition, the amino acid sequence of cetuximab may consist of the heavy chain of SEQ ID NO: 7 and the light chain of SEQ ID NO: 8.

In addition, the present invention provides a pharmaceutical composition for treating cancer comprising the antibody drug conjugate. Cancer in which the antibody drug conjugate of the present invention shows a therapeutic effect may be one or more selected from the group consisting of head and neck cancer, colon cancer, lung cancer, breast cancer, prostate cancer, renal cancer, pancreatic cancer, ovarian cancer, brain cancer or bladder cancer, etc. Preferably, the antibody drug conjugate consisting of tetravalent conjugate comprising the bispecific cetuximab×anti-cotinine and bivalent cotinine binding peptide cross-linked with duocarmycin (cotinine-duocarmycin) of the present invention shows a significant therapeutic effect for KRAS mutation lung adenocarcinoma having primary resistance to EGFR targeted treatment of cetuximab. Preferably, the total amino acid sequence of the antibody drug conjugate consisting of the tetravalent conjugate comprising the bispecific cetuximab×anti-cotinine antibody and cotinine-duocarmycin may consist of the light chain sequence of SEQ ID NO: 9 and the heavy chain sequence of SEQ ID NO: 10.

The pharmaceutical composition of the present invention may be administered by various methods known in the art. The route or method of administration may be different according to the desired result, and it may be administered intravenously, intramuscularly, intraperitoneally or subcutaneously or closely to the targeted site. The antibody drug conjugate of the present invention may be formulated in pharmaceutically acceptable administration forms by common methods known to those skilled in the art.

In addition, the present invention provides a method for preparing an antibody drug conjugate comprising (s1) a step of preparing a bispecific antibody comprising an anti-cotinine single chain variable fragment (scFv); (s2) a step of preparing a conjugate of a bivalent cotinine which is cross-linked with a peptide and a drug; and (s3) a step of mixing the bispecific antibody produced in the (s1) step and the conjugate produced in the (s2) step. In the (s3) step, the anti-cotinine single chain variable fragment and bivalent cotinine bind specifically, thereby preparing the antibody drug conjugate. In addition, the bivalent cotinine, in which two cotinines are cross-linked to the N-terminus and C-terminus of a 6~18 mer peptide, may be used. In addition, the preparation method may comprise a) a step of inserting a nucleic acid molecule encoding the anti-cotinine scFv-combined bispecific antibody into a vector; b) a step of introducing the vector into a host cell; and c) a step of culturing the host cell.

Moreover, the present invention provides a method for treating cancer comprising a step of treating an effective dose of the antibody drug conjugate into an animal. Furthermore, the present invention provides a use for preparing the pharmaceutical composition for treating cancer of the antibody drug conjugate of the present invention.

The method for treating cancer of the present invention may comprise administering the composition comprising the antibody drug conjugate of the present invention in a therapeutically effective dose. Herein, the term of "therapeutically effective dose" represents the amount of the antibody drug conjugate or composition comprising it of the present invention effective for prevention or treatment of cancer-related diseases.

The actual dose level of the antibody drug conjugate in the pharmaceutical composition of the present invention may be different so as to reach the effective amount of the active ingredient for achieving the desired therapeutic reaction for specific patient, composition and administration method, which is not toxic to the patient. The dose level may be different according to various pharmacodynamic factors, for example, activity of the used antibody drug conjugate of the present invention, administration route, administration time, emission rate of used conjugate, treatment period, other drug, compound or material used with the conjugate, age, gender, body weight, condition, common health and previous medical history of patients to be treated, or other factors, etc.

Herein, the treatment dose of the pharmaceutical composition may be titrated to optimize stability and efficacy. When the antibody drug conjugate of the present invention is systemically administered, the dose range may be in the range of about 0.0001 to 100 mg per host body weight 1 kg, more commonly 0.01 to 15 mg. For example, the treatment method may accompany systemic administration once per two weeks, or once per month, or once per 3 months to 6 months.

In addition, the present invention provides a method for enhancing a half-life of a drug through the antibody drug conjugate. In the experimental example 3 of the present invention, when the conjugate with ERC6 was formed, the pharmacokinetic analysis was performed to evaluate the stability of cotinine payloads. As the experimental result, it was confirmed that the cotinine payloads were rapidly removed in the blood stream due to its low molecular weight, but on the other hand, when it combined to ERC6, the half-life was extended. Furthermore, the antibody drug conjugate of the present invention can significantly enhance the stability of the conjugate compared to the single cotinine-drug conjugate, by using the bivalent cotinine cross-linked to the peptide.

Herein, "antibody" means a substance produced by stimulus of an antigen in the immune system, and its kind is not particularly limited. Herein, the antibody may include an animal antibody, chimeric antibody, humanized antibody or complete human antibody all. In addition, herein, the antibody may include a fragment of the antibody having the antigen binding capacity, for example, Fab. The chimeric antibody means an antibody in which the antibody variable region or its complementary determining region (CDR) is derived from the different animal from the other parts of the antibody. This antibody may be an antibody in which the antibody variable region is derived from an animal other than human (for example, mouse, rabbit, poultry, etc.), and the antibody invariable region is derived from human. This chimeric antibody may be prepared by methods such as gene recombination, etc. known in the art.

Herein, "heavy chain" refers to a full-length heavy chain comprising a variable domain $V_H$ comprising an amino acid sequence of a variable region enough to provide specificity to an antigen and 3 invariable region domains, $C_H1$, $C_H2$ and $C_H3$ and its fragment all. In addition, "light chain" refers to a full-length light chain comprising a variable domain $V_L$ comprising an amino acid sequence of a variable region enough to provide specificity to an antigen and an invariable region domain $C_L$ all.

Herein, "conjugate" means a heterologous molecule and may be produced by covalently attaching one or more polypeptide(s), typically one polypeptide, to one or more non-polypeptide part(s), particularly a polymer part, such as a polymer molecule, a lipophilic compound, a carbohydrate part, and an organic derivatizing agent. Additionally, the conjugate may be attached to one or more carbohydrate parts, particularly, using N- or O-glycosylation. The meaning of attaching covalently means directly binding polypeptide and non-polypeptide parts covalently each other, or covalently linking them indirectly each other through a cross bridge, space, linking part or mediating part, etc. For example, the conjugate conjugating the drug disclosed herein with cotinine is included in the present definition.

In addition, the present invention provides an in vitro biological analysis method, wherein the conjugate of cotinine and drug is used as an analysis tool. The in vitro biological analysis method may be selected from the group consisting of cell cytometry, western blot analysis, immunoprecipitation analysis and enzyme-linked immunochemical analysis, etc.

The conjugate in which the anti-cotinine antibody is combined to the conjugate of drug and cotinine according to the present invention may retain all unique characteristics of the drug and antibody by using the cotinine as a hapten. Specifically, the antibody drug conjugate of the present invention may retain specific reactivity and functions of the molecule, and complement-mediated cytotoxicity (CDC), antibody-dependent cytotoxicity (ADCC) and long in vivo half-life that are characteristics of the antibody.

Advantageous Effects

The antibody drug conjugate of the present invention can effectively deliver a drug to a target to which an antibody specifically binds, and enhance the half life of the drug in body, thereby improving therapeutic effects. In particular, the bispecific conjugate of the bivalent cotinine-peptide conjugated with cetuximab×anti-cotinine antibody and duocarmycin shows the significant anti-tumor activity to EGFR-positive cetuximab refractory lung adenocarcinoma having KRAS mutations.

In addition, the antibody drug conjugate platform of the present invention does not require optimization of the antibody, and a cytotoxic agent is conjugated to the interested antibody through simple culture, and thereby multistep complex conjugation procedures can be largely reduced. In other words, the antibody drug conjugate platform of the present invention can be used for overcoming limitations of conventional ADCs and ultimately developing more effective therapeutic agents hereafter.

BRIEF DESCRIPTION OF THE DRAWINGS

FIG. 1a is a schematic diagram of the antibody drug conjugate (ADC) using the bispecific antibody. The bispecific (cetuximab×anti-cotinine) antibody (ERC6) is designed to have binding specificity to both human EGFR and cotinine payloads. FIG. 1b shows the SDS-polyacrylamide gel electrophoresis (SDS-PAGE) result. The purified ERC6 was inserted to 4-12% (w/v) SDS-PAGE. Bands were visualized by staining the gel with Coomassie Brilliant Blue. The lane 1 or 2 is a sample with or without a reducing agent, respectively. FIG. 1c is size-exclusion chromatography (SEC). The purified ERC6 was analyzed through SEC using high pressure liquid chromatography (SEC-HPLC). FIG. 1d show the pharmacokinetic analysis result of ERC6. 200 μg ERC6 was intravenously injected to Balb/c mice (n=4), and the blood sample was collected through the vein in the orbit of the eye. The circulating serum level of ERC6 was analyzed by enzyme-linked immunosorbent analysis (ELISA). The result was shown as mean±SD obtained from the experiments performed three times.

FIG. 2a shows the enzyme immunoassay result. Cetuximab, anti-cotinine-IgG and ERC6 were added to wells of a microtiter plate coated with human EGFR or cotinine. The wells were probed with HRP-complexed anti-human IgG (Fab-specific) antibody. FIG. 2b shows the chemical structure of the cross-linked dPEG6 biotin and bivalent cotinine-conjugated peptide (cotinine-biotin). FIG. 2c is the result of adding cetuximab, anti-cotinine-IgG and ERC6 to other wells of the microtiter plate coated with human EGFR and then adding cotinine-biotin and detecting wells with HRP-conjugated streptavidin. The background signal was measured in control wells coated with BSA. The absorbance was measured at 650 nm. FIG. 2d shows the pharmacokinetic analysis of ERC6-complexed cotinine-biotin. 200 μg ERC6 pre-cultured with 1.85 μg cotinine-biotin dissolved in 100 μL sterile PBS was intravenously injected to Balb/c mice (n=4). The blood sample was collected through the vein in the orbit of the eye and the circulating serum level of the ERC6-complexed cotinine-biotin was measured by ELISA. The result was shown as mean±SD obtained from the experiments performed three times.

FIG. 3a is the flow cytometry result. With or without cotinine-biotin, A549 cells were cultured with cetuximab, anti-cotinine-IgG or ERC6. For analysis, the cells were detected with PE-conjugated streptavidin and FITC-conjugated anti-human Fc. FIG. 3b shows the structure of free duocarmycin. FIG. 3c shows the chemical structure of the bivalent conjugated peptide cross-linked with four duocarmycins (cotinine-duocarmycin). R represents valine-citrulline PAB-linked dimethyl aminoethyl duocarmycin. FIG. 2d is the cell viability analysis result of free duocarmycin. FIG. 3e is the cell viability analysis result of cotinine-duocarmycin. The A549 cell line was treated with palivizumab and DMSO (●); cetuximab and DMSO (■); ERC6 and DMSO (▲); palivizumab and duocarmycin (○); cetuximab and duocarmycin (□); ERC6 and duocarmycin (Δ). Palivizumab was used as the isotype control of bispecific antibody. DMSO was used as the vehicle control of cotinine-duocarmycin. After culturing cells for 72 hrs, the cell ATP content was measured using Cell Titer-Glo reagent, thereby measuring the relative cell viability. The result was shown as mean±SD obtained from the experiments performed three times.

FIG. 4a is the result of measuring the tumor volume for 32 days, FIG. 4b is the result of observing the body weight during the treatment period. FIG. 4c is the average tumor volume at the day 32. FIG. 4d is the average mass of dissected tumor when mice were sacrificed. FIG. 4e shows the photograph of tumor of three treatment groups at the end point. The result was shown as mean±SD; compared with the group, *P<0.05, **P<0.01, Student's t test.

FIG. 6 shows the anti-proliferative effect of the ERC6-complexed cotinine-DM1 (emtansine) in the EGFR-positive lung adenocarcinoma cell line.

DETAILED DESCRIPTION

Figure 1A:
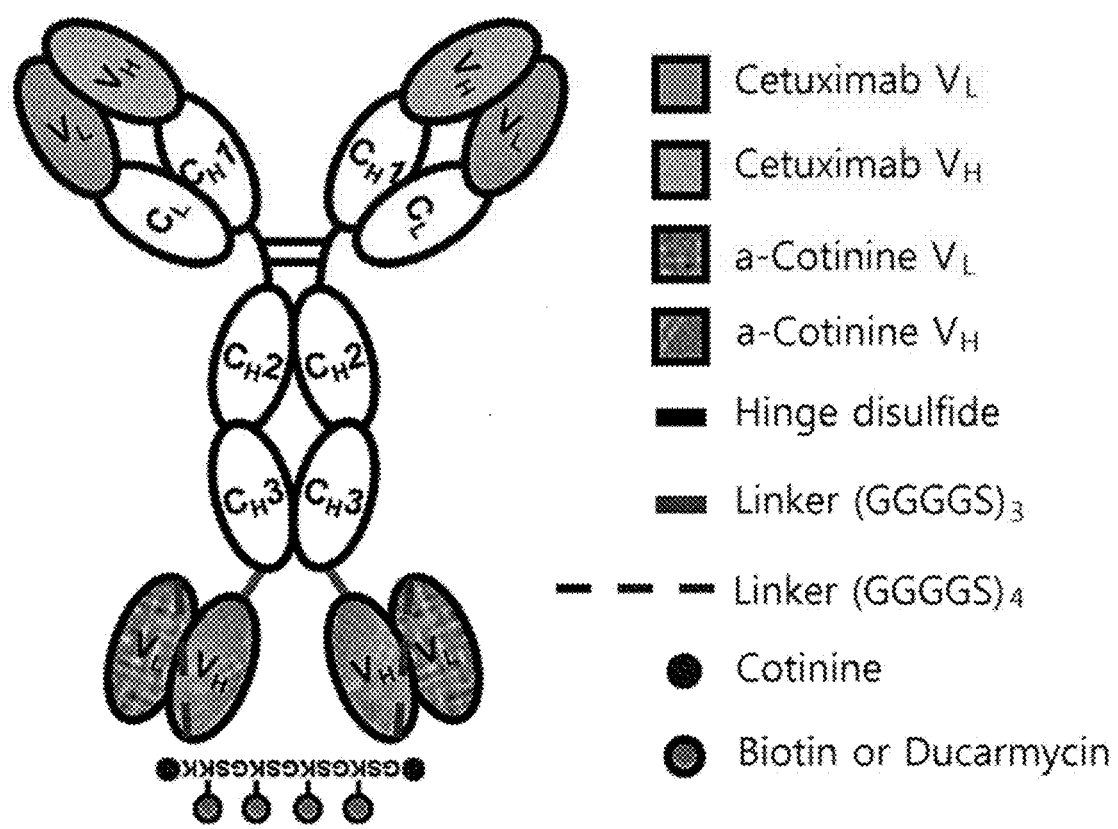
FIGS. 1a, 1b, 1c and 1d show production and characteristics of bispecific (cetuximab×anti-cotinine) antibody (ERC6).

Hereinafter, examples, etc. will be described in detail to facilitate understanding of the present invention. However, the examples according to the present invention can be modified into various other forms, and the scope of the present invention should not be construed as being limited to the following examples. The examples of the present invention are provided to enable those skilled in the art to more completely understand the present invention.

Example 1: Cell Culture

A549 (human lung adenocarcinoma) cells were obtained from the Korean Cell Line Bank and grown in RPMI-1640 media (Welgene, Seoul, Republic of Korea) supplemented with 10% heat inactivated fetal bovine serum (GIBCO, Grand Island, N.Y., USA), 100 U/mL penicillin, and 100 μg/mL streptomycin in a humidified atmosphere with 5% $CO_2$. HEK293F cells (Invitrogen, Carlsbad, Calif., USA) were grown in FreeStyle™ 293 Expression medium (GIBCO), containing 100 U/mL penicillin and 100 μg/mL streptomycin in Erlenmeyer tissue culture flask with vent cap (Corning Inc., NY, USA) at 37° C. in 70% humidified atmosphere with 7% $CO_2$ in an orbital shaking incubator (Minitron, INFORS HT, Bottmingen, Switzerland) at 135 rpm.

Example 2: Construction and Purification of Bispecific Cetuximab×Anti-Cotinine Antibody To construct bispecific cetuximab×anti-cotinine antibody expression vector, genes encoding cetuximab light chain and cetuximab heavy chain-linker(Gly-Gly-Gly-Gly-Ser)$_3$-anti-cotinine single chain variable fragment (scFv) were chemically synthesized (Genscript, Picataway, N.J., USA). Restriction sites, AgeI and XbaI were inserted at the 5' and 3' ends of the gene encoding cetuximab light chain, respectively. Additional restriction sites, NheI and BsiWI were inserted at the 5' end of the gene encoding cetuximab heavy chain and the 3' end of the gene of anti-cotinine scFv. Light chain and heavy chain-linker-anti-cotinine-scFv was subcloned into mammalian expression vector designed for secretion of recombinant protein as the method described in Park S, Lee D H, Park J G, Lee Y T, Chung J. A sensitive enzyme immunoassay for measuring cotinine in passive smokers. *Clin Chim Acta* 2010; 411(17-18): 1238-42.

As the method described in Boussif O, Lezoualc'h F, Zanta M A, Mergny M D, Scherman D, Demeneix B et al. A versatile vector for gene and oligonucleotide transfer into cells in culture and in vivo: polyethylenimine. *Proc Natl Aced Sci USA* 1995; 92(16): 7297-301, the expression vector encoding ERC6 was transfected into HEK293F (Invitrogen) using 25-kDa linear polyethyleneimine (Polyscience, Warrington, Pa., USA). As the method described in Kim H, Park S, Lee H K, Chung J. Application of bispecific antibody against antigen and hapten for immunodetection and immunopurification. *Exp Mol Med* 2013; 45: e43, the ERC6 was purified from the culture supernatant by affinity chromatography using protein A agarose bead (RepliGen, Waltham, Mass., USA).

Example 3: Sodium Dodecyl Sulfate-Polyacrylamide Gel Electrophoresis (SDS-PAGE)

The analysis was performed by sodium dodecyl sulfate-polyacrylamide gel electrophoresis (SDS-PAGE) using NuPage 4-12% Bis-Tris gel (Invitrogen) according to the manufacturer's instructions. The gel was stained with Coomassie Brilliant Blue R-250 (Amresco, Colon, Ohio, USA).

Example 4: Size-Exclusion Chromatography (SEC)

Purified ERC6 was analyzed by SEC-HPLC, using Agilent 1260 Infinity high pressure liquid chromatography (HPLC) system equipped with Bio SEC-3 column (7.8×300 mm) packaged with 3 μm particles containing *57300 Å pores (Agilent 1260, Agilent technologies Inc., CA, USA). The mobile phase comprised 50 mM sodium phosphate and 150 mM sodium chloride of pH 7.0. 20 μL of ERC6 (1 mg/ml) was injected and eluted isocratically at the flow velocity of 1 mL/min for 30 min. The column effluence was monitored with a ultraviolet ray detector at 280 nm and represented as mAU. The percentage of monomers, aggregates and fragments was quantified on the basis of peak area.

Example 5: Synthesis of Cotinine Conjugates

All peptides used in the present experiment were chemically synthesized using Fmoc-solid-phase peptide synthesis (Peptron, Republic of Korea). Two trans-4'-cotininecarboxylic acids (Sigma-Aldrich, St Louis, Mo., USA) were cross-linked to free amine groups at the N-terminus and C-terminus of GGGGSKGGGGSK and GSKGSKGSKGSKK peptides. After eliminating the allyloxycarbonyl (alloc) group on lysine at the middle of peptides with triphenylphosphine (tetrakis) palladium, dPEG6 (Peptide international Inc., Louisville, Ky., USA) was conjugated to free amine group of GGGGSKGGGGSK peptide. Then, biotin was cross-linked to free amine on dPEG6-conjugated peptide (Peptron). For simplification, the bivalent cotinine-conjugated peptide cross-linked with biotin (cotinine-GGGGSK[(dPEG6)-biotin]GGGGSK-cotinine) was abbreviated to cotinine-biotin.

Four valine-citrulline PAB-linked dimethyl aminoethyl duocarmycins were conjugated to free amino acid groups present in 4 lysines in bivalent cotinine-cross-linked GSKG-SKGSKGSKK peptide (Concortis, San Diego, Calif., USA). For simplification, the bivalent cotinine-conjugated peptide cross-linked with 4 duocarmycins (cotinine-[GSK(duocarmycin)]$_4$K-cotinine) was abbreviated to cotinine-duocarmycin.

The cotinine-biotin and cotinine-duocarmycin were purified via reverse-phase using a C18 column. After purification, they were analyzed and validated by mass spectrometry using Agilent 1100 capillary LC and HPLC system equipped with Capcell Pak C18 column (4.6×50 mm, 120 Å) (Shimadzu Corp., Kyoto, Japan).

Example 6: Complexation of ERC6 and Cotinine Payloads

To produce complexes of ERC6 and cotinine-conjugated payloads, the cotinine payloads and ERC6 were mixed though pipetting up and down at the molar ratio of 1:1. Then, the mixture was cultured at the room temperature for 30 min. Then, the complexes were used in vitro or in vivo without additional modifications.

Example 7: Enzyme-Linked Immunosorbent Assay (ELISA)

The wells of a 96-well microtiter plate (Corning) were coated with human EGFR (Sigma) or BSA-conjugated cotinine in coating buffer (0.1M sodium bicarbonate in distilled water, pH 8.6) overnight at 4° C. and blocked with 3% bovine serum albumin (BSA) in PBS for 1 h at 37° C. The antibody at concentrations of 1 μg/mL in 50 μL blocking buffer was added to each well and incubated for 2 hrs at 37° C. After washing with 0.05% Tween 20 in PBS (PBST), HRP-conjugated anti-human IgG (Fab specific) antibodies (Sigma) diluted in the blocking buffer was added and incubated for 1 hr at 37° C. Then, after washing the plate again with 0.05% PBST, 50 μL 3,3',5,5'-tetramethyl benzidine substrate solution (TMB) (GenDEPOT, Barker, Tex., USA) was added to each well, and the absorbance was measured at 650 nm with a Multiskan Ascent microplate reader (Labsystems, Helsinki, Finland).

To confirm bispecificity of ERC6, the human EGFR-coated wells were cultured with antibodies as above. After washing with 0.05% PBST, the cotinine-biotin was added to each well and cultured for 1 hr at 37° C. Then, HRP-conjugated streptavidin (Thermo Fishers Scientific, Waltham, Mass., USA) diluted in the blocking buffer was added and incubated for 1 hr at 37° C. After washing, TMB was added to each well, and the absorbance was measured at 650 nm.

Example 8: Pharmacokinetic Analysis

All the animals used in the present experiment was reviewed and approved by Institutional Animal Care and Use Committee (IACUC) of National Cancer Center Research Institute, Republic of Korea (Permit number: NCC-15-267). The animals were maintained in the National Cancer Center animal facility in accordance with the AAALAC International Animal Care Policy.

Eight-week-old male Balb/c mice were intravenously injected with the complex of ERC6 (200 μg) and cotinine-biotin (1.85 μg) in one-to-one molar ratio dissolved in 100 μL sterile PBS (n=4/group). Blood samples were collected from intra-orbital vein at 0, 1, 24, 48, 72, 96 and 168 hrs post-injection. The samples were left at the room temperature for 2 hrs until the blood coagulated. Subsequently, serum was acquired by centrifuging at 3500 rpm for 15 min at 4° C. The circulating serum levels of total ERC6 and ERC6-complexed cotinine-biotin were determined by enzyme-linked immunosorbent assays (ELISAs).

Total ERC6 in the serum samples was measured as follows: the wells of a 96-well microtiter plate (Corning) were coated with goat anti-human IgG (Fc specific) capturing antibody (EMD Millipore, Darmstadt, Germany) in coating buffer overnight at 4° C. and blocked with 3% BSA in PBS for 1 hr at 37° C. Serum samples diluted in blocking buffer and standard solution were added to each well and incubated for 2 hrs at 37° C. After washing with 0.05% PBST, HRP-conjugated anti-human $C_{kappa}$ antibody (Thermo Fisher Scientific, Waltham, Mass., USA) diluted in the blocking buffer was added and incubated for 1 hr at 37° C. After washing, TMB (GenDEPOT) was added to each well and the absorbance was measured at 650 nm.

The complex of ERC6 and cotinine-biotin in the serum samples was measured as follows: the wells coated with human EGFR (Sigma) were cultured with serum samples as aforementioned. After washing with 0.05% PBST, HRP-conjugated streptavidin (Thermo Fisher Scientific Pierce) was added and cultured for 1 hr at 37° C. After washing, TMB was added to each well and the absorbance was measured at 650 nm.

Example 9: Flow Cytometry

A549 cells were seeded in a v-bottom 96-well plate (Corning) in the final concentration of $4×10^5$ cells per each sample. The cells were treated with 0 or 100 nM of ERC6 and cotinine-biotin diluted in the flow cytometry buffer (0.1% [w/v] sodium azide containing 1% [w/v] BSA in PBS) for 30 min at 37° C. For control experiments, instead of ERC6, palivizumab (Synagis, Boehringer Ingelheim Pharma, Biberach an der Riss, Germany), anti-cotinine-IgG or cetuximab (Erbitux, Merck K GaA, Darmstadt, Germany) was used. After washing with the flow cytometry buffer, the cells were cultured with phycoerythrin (PE)-conjugated streptavidin (BD Biosciences Pharminogen, San Diego, Calif., USA) and FITC-conjugated anti-human IgG (Fc specific) antibody (Thermo Fisher Scientific Pierce) in the dark for 1 hr at 37° C. After additional washing with the same buffer, the cells were resuspended in 200 μL PBS, and analyzed through flow cytometry using FACS Canto II instrument equipped with a 488-nm laser (BD Bioscience, San Jose, Calif., USA). 10,000 cells per measurement were detected and data were analyzed with FlowJo software (TreeStar, Ashland, Oreg., USA).

Example 10: Cell Viability Assays

The effect of ERC6 and cotinine-duocarmycin on tumor cell viability was evaluated using Cell Titer-Glo reagent (Promega Corp., Madison, Wis., USA). A549 cells were seeded in 50 μL RPMI-1640 medium in black-walled 96-well plates (4,000 cells per well) and allowed to adhere overnight at 37° C. in 5% $CO_2$ and humidified atmosphere. Subsequently, the complexes of ERC6 and cotinine-duocarmycin were serially diluted 10-fold in fresh culture medium (0.02 nM-2000 nM). In the control experiments, instead of ERC6, palivizumab (Boehringer Ingelheim Pharma), or cetuximab (Merck K GaA) was used. The cotinine-duocarmycin and antibody dilutes in 50 μL medium were added to each well, and cultured for 72 hrs. After adding Cell Titer-Glo reagent (Promega Corp.) to each well, luminescence signals were measured using a microplate luminometer (PerkinElmer, Waltham, Mass., USA) according to the manufacturer's instructions. All experiments were conducted in triplicate. The relative cell viability was calculated by dividing by the control luminescence signal [% viability= (Test−Background)/(Control−Background)×100].

Example 11: Xenograft

Six-week-old female Balb/c-nude mice were subcutaneously injected with the A549 ($1\times10^7$ cells) on the left and right flank of each mouse. When the tumor volume reached approximate 150 mm$^3$, all animals were randomly divided into three groups (n=4/group) and treated for five weeks. Mice were intraperitoneally injected with appropriate controls twice a week for the first two weeks: Group I was administered with palivizumab (2.15 mg/kg) and cotinine-duocarmycin (95 μg/kg); Group II was administered with the ERC6 (3 mg/kg) and dimethyl sulfoxide (DMSO); Group III was administered with the complex of ERC6 (3 mg/kg) and cotinine-duocarmycin (95 μg/kg). Then, three times dose of the drugs were injected thrice a week for the following three weeks. Palivizumab was used as an isotype control of the bispecific antibody. DMSO was used as a vehicle control of cotinine-duocarmycin. The tumor volume was measured using digital calipers twice a week in 32 days after injection. Tumor volume was calculated as length×(width)$^2$×0.5, where the length is the longest axis and the width is the distance perpendicular to the length. Systemic toxicity was evaluated by measuring body weight twice a week. Mice were sacrificed on the day 35 after injection and tumors were dissected and weighted.

Example 12: Immunofluorescence

Balb/c-nude mice were subcutaneously injected with the A549 ($1\times10^7$ cells) on the left and right flank. When the tumor volume reached 500 mm$^3$, mice having tumors were administered by the following single intraperitoneal (i.p.) injection: Group I was administered with 144 μg palivizumab and 1.85 μg cotinine-biotin; Group II was administered with 200 μg ERC6 and vehicle (distilled water); Group III was administered with the complex of ERC6 (200 μg) and cotinine-biotin (1.85 μg). In 24 hrs after injection, mice were anesthetized with isoflurane and euthanized through transcardial perfusion with 10 ml of 4% [w/v] paraformaldehyde in PBS. The dissected tumors were equilibrated in cryopreservation solution containing 30% [w/v] sucrose in PBS for 24 hrs at 4° C., and frozen in the optimum cutting temperature embedding medium (Sakura Finetek, Torrance, Calif., USA) in liquid nitrogen, and stored at −80° C. until cutting. For immunofluorescent staining, cryosections were prepared in 4 μm thickness, and fixed with 4% paraformaldehyde in PBS for 10 min at the room temperature. After washing with PBS, the sections were blocked with 10% [v/v] normal goat serum (CST, Danvers, Mass., USA) in IHC-Tek antibody diluted solution (pH 7.4) (IHC WORLD, Woodstock, Md., USA) for 1 hr at the room temperature. The tissue sections were cultured with Alexa Fluor 488-conjugated streptavidin (Molecular Probes Inc., Eugene, Oreg., USA for 8 hrs, and stained with Alexa Fluor 594-conjugated anti-human IgG antibody (Molecular Probes Inc.) in the dark and humidified chamber of 4° C. for 16 hrs. After washing with PBS, nuclei were stained with 4',6-diamidino-2-phenylindole (DAPI; Pierce, Rockford, Ill., USA) according to the manufacturer's instructions. The sections were fixed on slides with fluorescence fixed medium (DAKO, Glostrup, Denmark) and 40-fold enlarge images were obtained with FV10 ASW software using FV1000 laser scanning microscope (Olympus, Tokyo, Japan). The emission and excitation filters were arranged so as to be imaged in three colors.

Statistical Analysis

Statistics used in the experiments were carried out using GraphPad Prism version 5.0 software (GraphPad Software Inc., San Diego, Calif., USA). Results were expressed as mean values of ±standard deviations (SD) for the indicated number of independent measurements. Statistical significance was determined using two tailed unpaired Student's t-test and P-values of less than 0.05 were considered statistically significant. P values are indicated in the figures and in their legends.

Experimental Example 1: Design of Antibody Drug Conjugate Platform Using Tetravalent Bispecific Antibody Format Bispecific antibodies were designed in the IgG-based tetravalent format by fusing two single chain variable fragments (scFvs) to $C_H3$ domain of heavy chain (FIG. 1a). For flexibility, the glycine and serine rich peptide linker [(Gly-Gly-Gly-Gly-Ser)$_3$] was inserted between the $C_H3$ domain and scFv. Hereby, the tetravalent antibodies containing 2 of Fab arms of bispecific antibody and 2 of scFvs of C-terminus of heavy chain were produced, thereby simultaneously targeting epidermal growth factor receptor (EGFR) and cotinine, respectively. To develop bispecific cetuximab×anti-cotinine scFv antibodies (ERC6), the gene structure encoding cetuximab IgG, linker and anti-cotinine scFv were cloned into the eukaryotic expression vector, ERC6 was purified from HEK393F culture supernatant transfected temporarily using protein A affinity column chromatography.

Figure 5A:
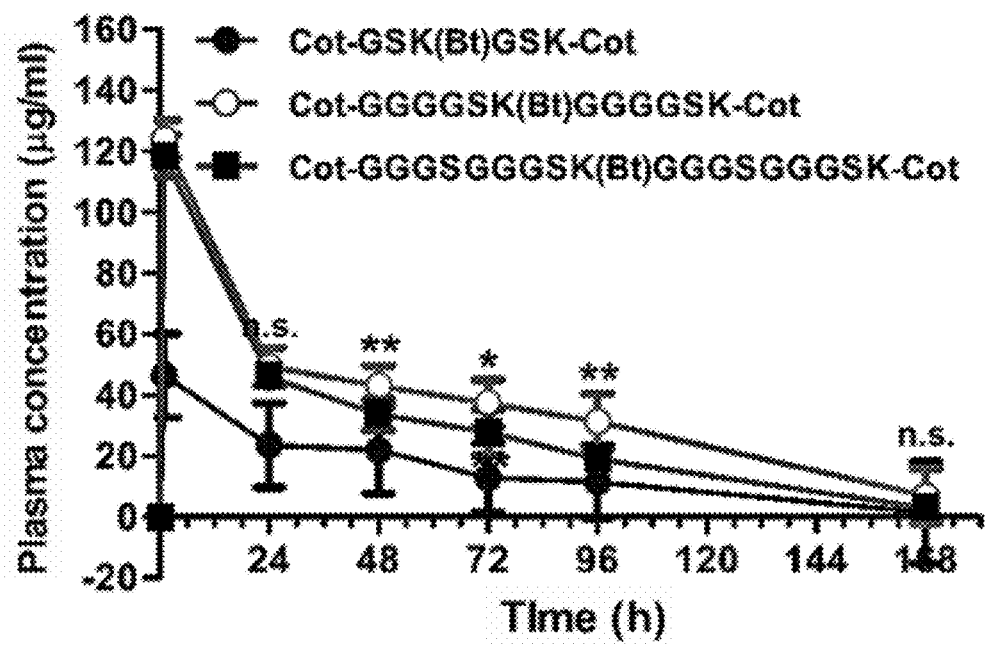
FIG. 5 is the pharmacokinetic analysis result of ERC6-complexed cotinine-biotin. (a) 200 μg of ERC6 pre-cultured with 964 pmole of cotinine-biotin dissolved in 100 μL sterile PBS at the molar ratio of 1:1 was intravenously injected to Balb/c mice (n=4). The peptide has various lengths of 6mer, 12mer or 18mer between two cotinine molecules. The blood sample was collected through the vein in the orbit of the eye, and the circulating serum level of the ERC6-complexed cotinine-biotin was determined by ELISA. (b) The circulating serum level of the total ERC6 was measured by ELISA. The result was shown as mean±SD; compared with the group, *P<0.05, **P<0.01, Student's t test.
Figure 5B:
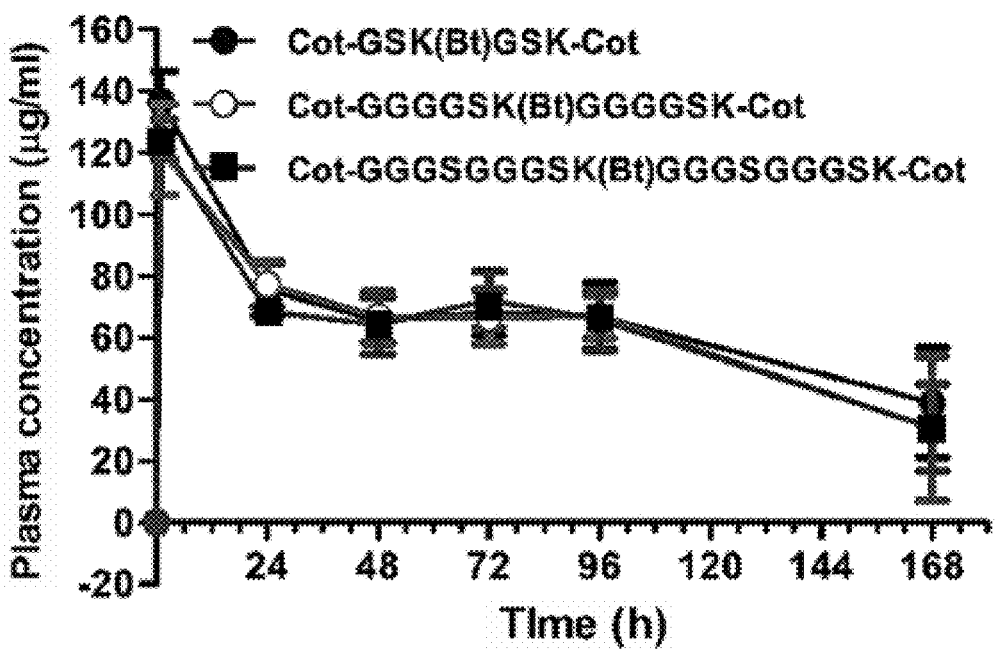

Conventional antibody drug conjugates require multistep procedures for conjugates to conjugate the drug to the antibody, and commonly the optimization procedure is necessary. On the other hand, the target delivery of drug using the cotinine-conjugated bispecific antibody requires conjugation of cotinine and drug. Thus, if the carboxycotinine (trans-4-cotininecarboxylic acid) chemical cross-link procedure is established, there will be an advantage for platform than conventional ADCs. Two carboxycotinines were cross-linked in N-terminus and C-terminus of the peptide in 13 amino acids length. The binding capacity of the bispecific antibody to the bivalent cotinine cross-linked peptide was more stable by the valency effect (FIG. 5). Various payloads can be conjugated to ε-amino acid chain of lysine in the peptide depending on purposes. In the present invention, biotin or duocarmycin was conjugated to the bivalent cotinine conjugated-peptide (FIG. 2b, 3c).

Experimental Example 2: Property of Bispecific Cetuximab×Anti-Cotinine scFv Antibody (ERC6)

Figure 1B:
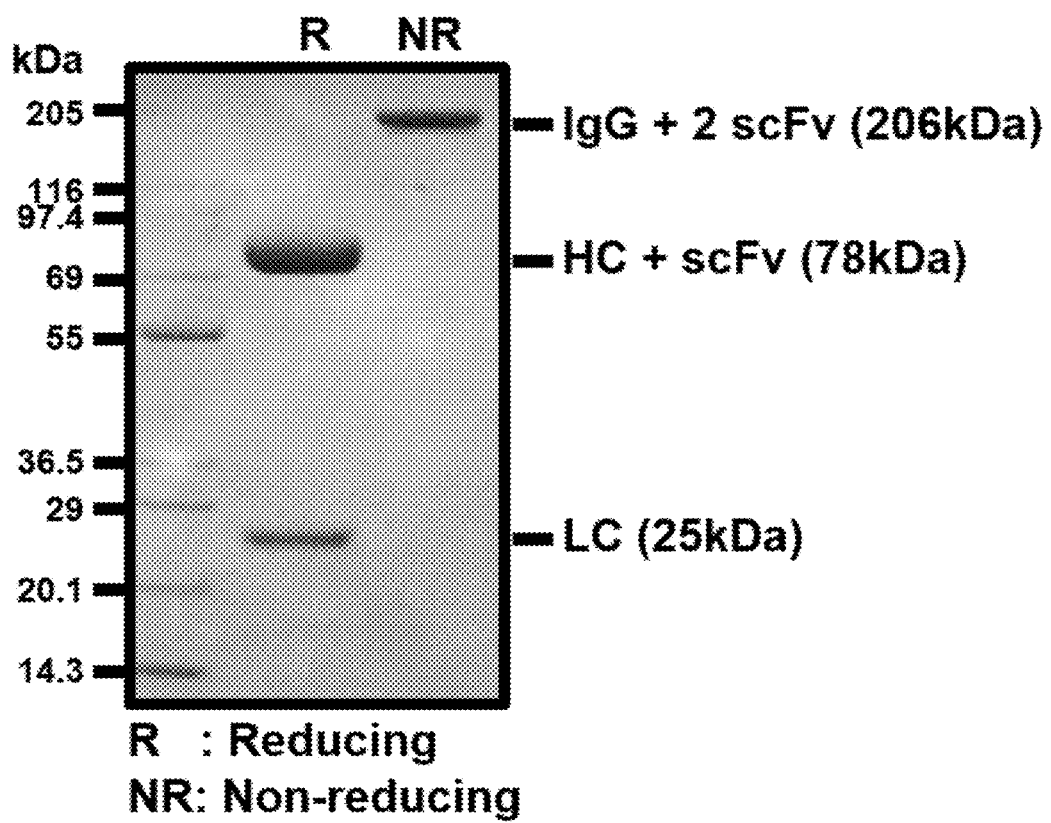

To analyze the purity and molecular weight of purified ERC6, ERC6 was visualized in a sodium dodecyl sulfate (SDS) polyacrylamide gel stained with Coomassie Brilliant Blue. The major band having the molecular weight of 206 kDa was observed in non-reducing condition, and two major bands of 78 kDa and 25 kDa were observed in non-reducing condition (FIG. 1b). The recombinant protein having the molecular weight of 206 kDa corresponded to the completely assembled ERC6, expected by ProtParam tool (ExPASy). The non-modified light chain of 25 kDa and the heavy chain fused with one scFv on the $C_H3$ domain of 75 kDa were visualized by reduction of disulfide bonds. Therefore, data demonstrated that bispecific antibodies were pure and prepared without damage.

Figure 1C:
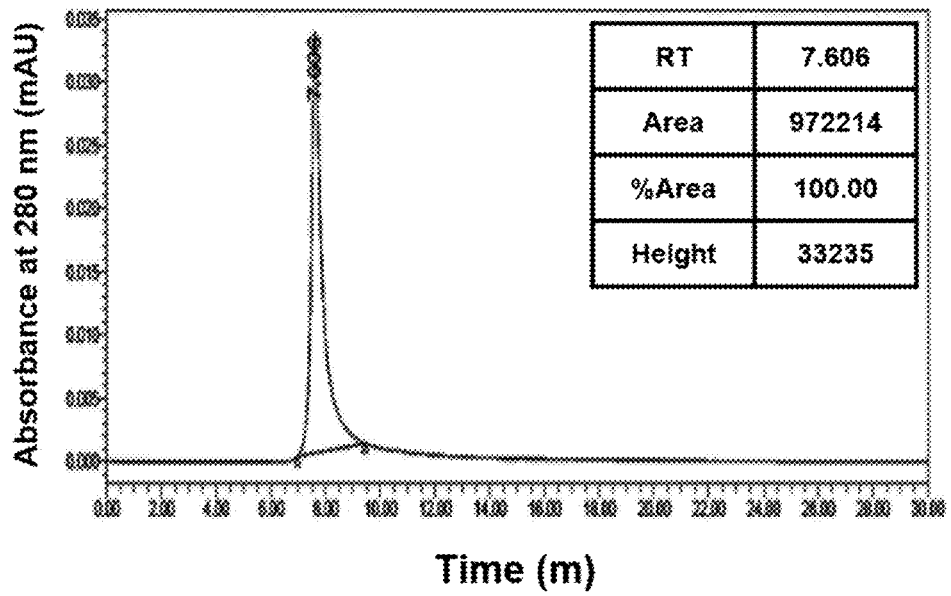
Figure 1D:
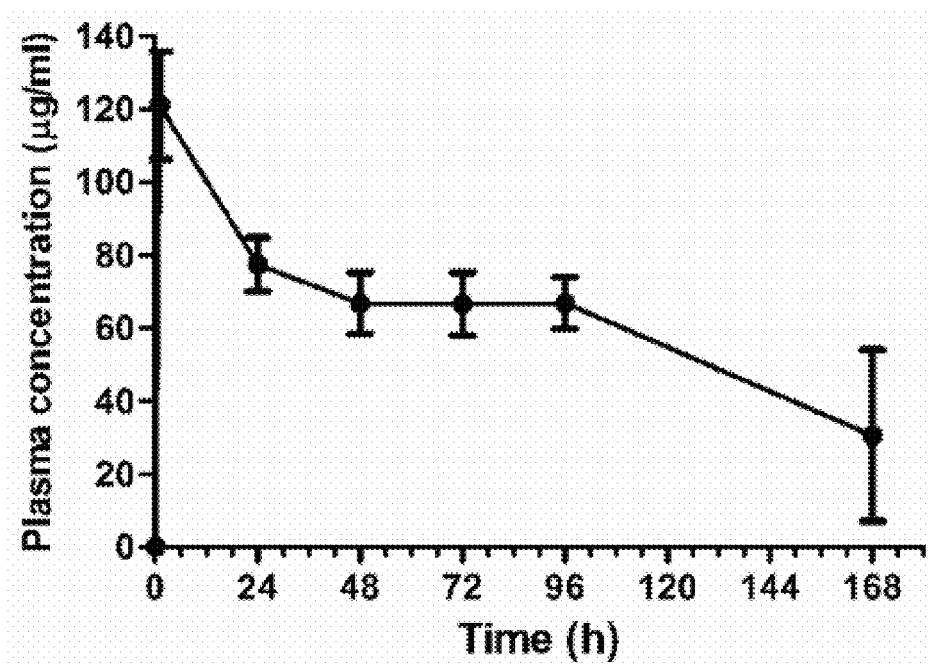

The physicochemical properties of purified recombinant protein were analyzed with size-exclusion chromatography using high pressure liquid chromatography (SEC-HPLC). The ERC6 was shown as the single major peak having the clear molecular weight corresponding to the rightly assembled form. These data showed that the ERC6 did not produce a fragment, and it was not aggregated, and it produced multi-mers (FIG. 1c).

In addition, to measure the stability of ERC6 in vivo, the pharmacokinetic analysis was performed. The serum half-life of ERC6 was determined in Balb/c mice (n=4). The circulating serum level of ERC6 was determined by enzyme-linked immunosorbent assay (ELISA) using blood samples collected from the vein in the orbit of an eye. The ERC6 intravenously injected was stable in the mouse serum until day 5, and this was similar to the result of cetuximab IgG.

Experimental Example 3: Binding Reactivity of ERC6 to Human EGFR and Cotinine

Figure 2A:
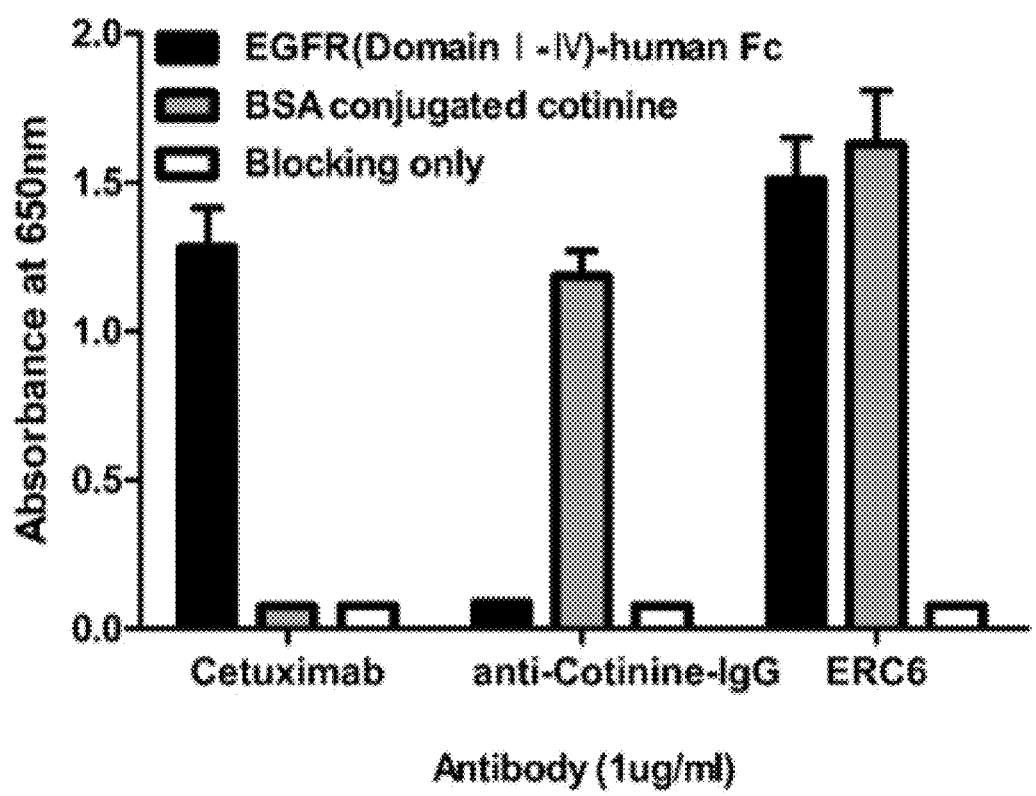
FIGS. 2a, 2b, 2c and 2d show the binding reactivity of ERC6 to human EGFR and cotinine.
Figure 2B:
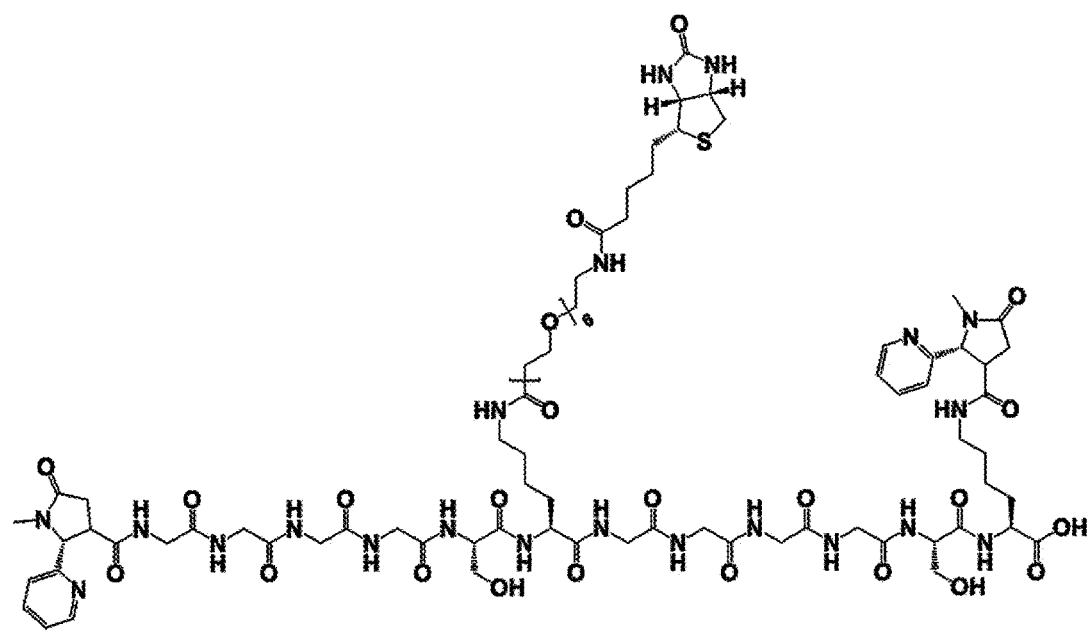

To experiment the reactivity of ERC6 to EGFR and cotinine, the enzyme immunoassay was applied (FIG. 2a). As the binding activity of ERC6 to EGFR was confirmed, it was demonstrated that the reactivity to EGFR was independent to an additional scFv. In addition, it was confirmed that the affinity of the anti-cotinine scFv module to cotinine was maintained (FIG. 2a).

Figure 2C:
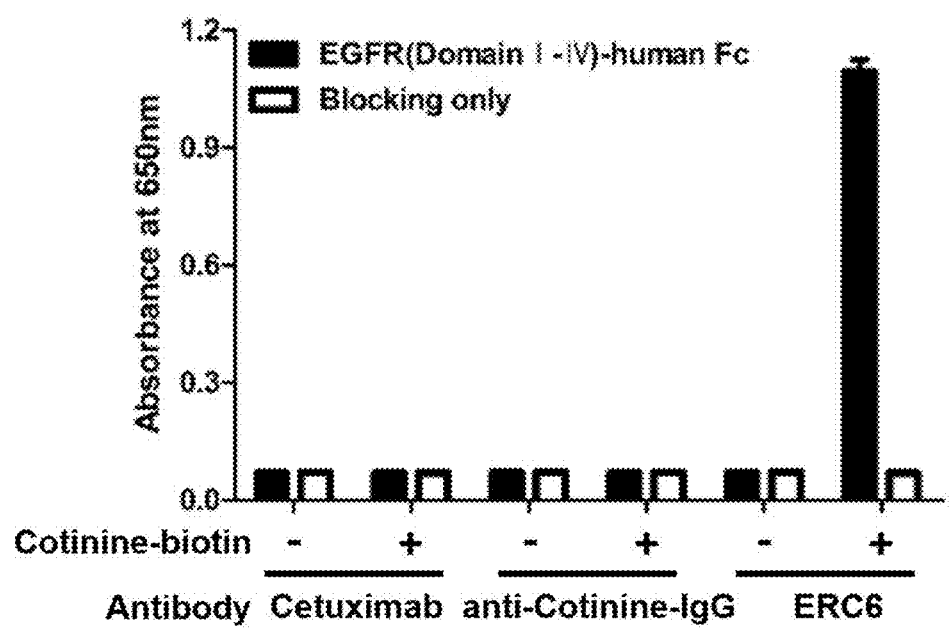

To determine whether ERC6 binds human EGFR and cotinine simultaneously, the additional enzyme immunoassay was performed using a streptavidin-biotin detection system. After culturing the human EFGR-coated microtiter plate with ERC6, the bivalent cotinine-conjugated peptide cross-linked with biotin (cotinine-biotin) was added to each well (FIG. 2b), and then the HRP-conjugated streptavidin was added. The ERC6 was simultaneously conjugated to EGFR and cotinine (FIG. 2c).

Figure 2D:
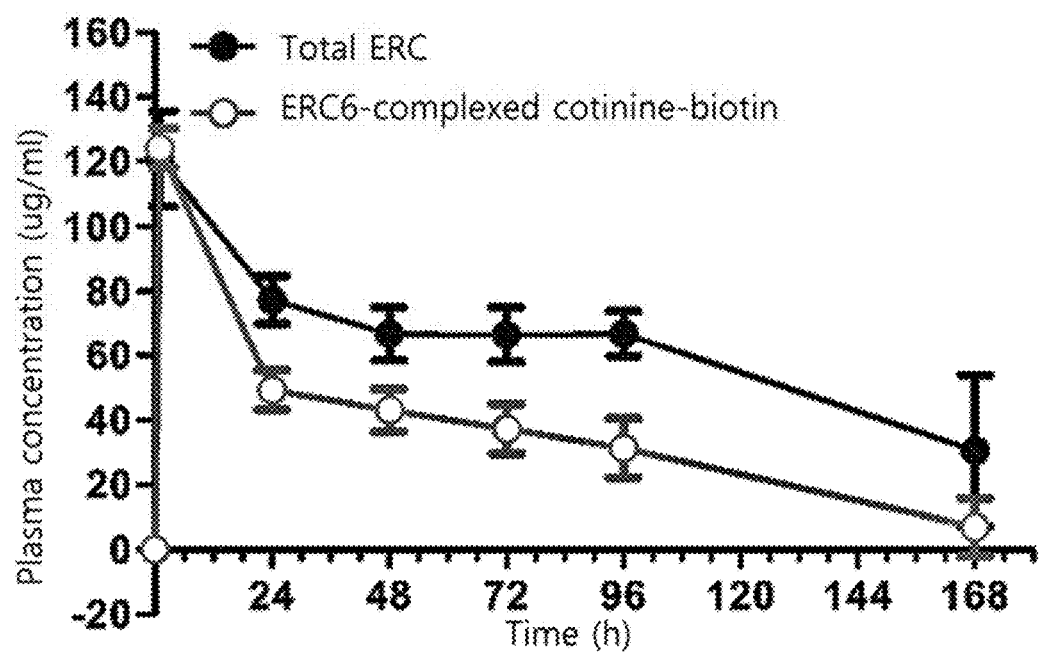
Figure 6A:
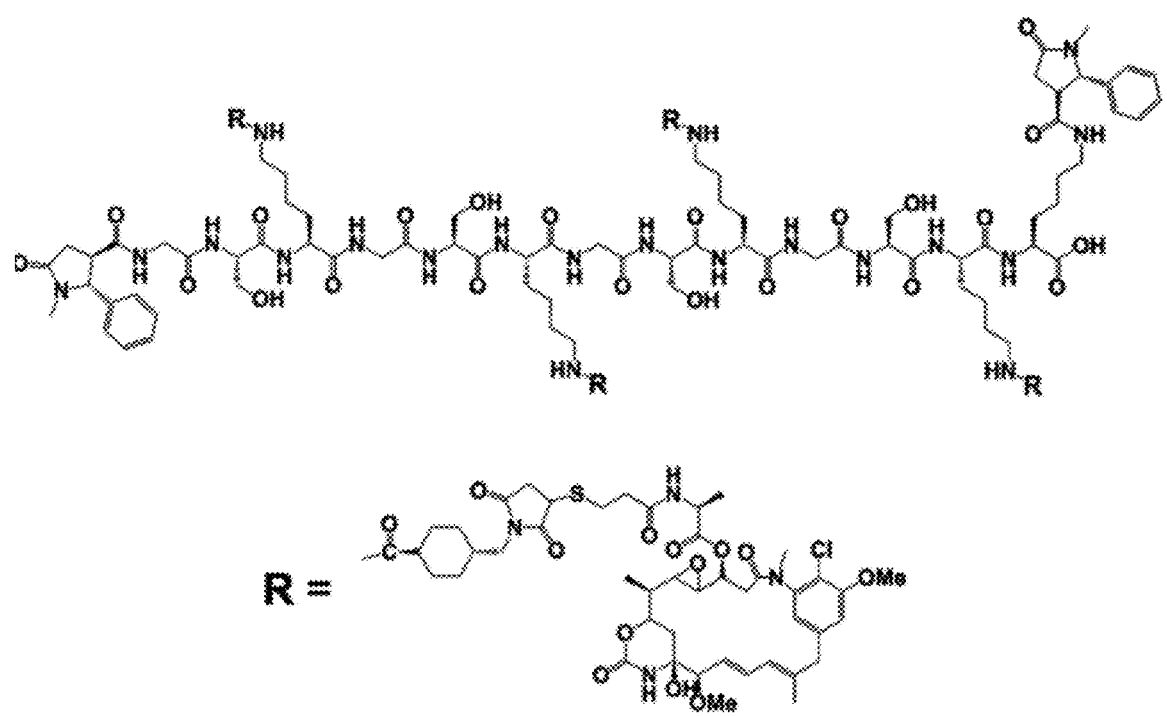
FIG. 6a shows the chemical structure of the bivalent cotinine-conjugated peptide cross-linked with four DM1s (cotinine-DM1). R represents MCC-linked DM1.

To evaluate the stability of cotinine payloads when forming the complex with ERC6, the pharmacokinetic analysis was performed. The ERC6 pre-cultured with cotinine-biotin was intravenously injected to mice (n=4) and the circulating serum level was measured by ELISA. The cotinine payload was rapidly removed in the mouse blood stream, due to its low molecular weight ($t_{1/2}$=0.557 h). On the other hand, the circulating half-life of the cotinine-biotin was extended by binding to ERC6 ($t_{1/2}$=18 hrs) (FIG. 2d). The duality of ERC6 to cotinine enhanced the stability of ERC6-complexed cotinine-biotin by increased binding capacity (FIG. 6). In addition, the clearance pattern of cotinine-biotin was matched with the decomposition pattern of ERC6, and this means that the half-life of the conjugate mostly depends on pharmacokinetics of ERC6 (FIG. 2d).

Experimental Example 4: ERC6-Complexed Cotinine-Duocarmycin Inducing Strong Cytotoxic Effect on Lung Adenocarcinoma Cells with KRAS Mutation A549 is a lung adenocarcinoma cell line that expresses wild-type EGFR with a KRAS mutation, showing primary resistance to EGFR targeted treatment such as cetuximab. Thus, to test the efficacy of ERC6-conjugated cotinine cytotoxic agent on cancer cells having wild-type EGFR and KRAS mutation, the cell line was used.

Figure 3A:
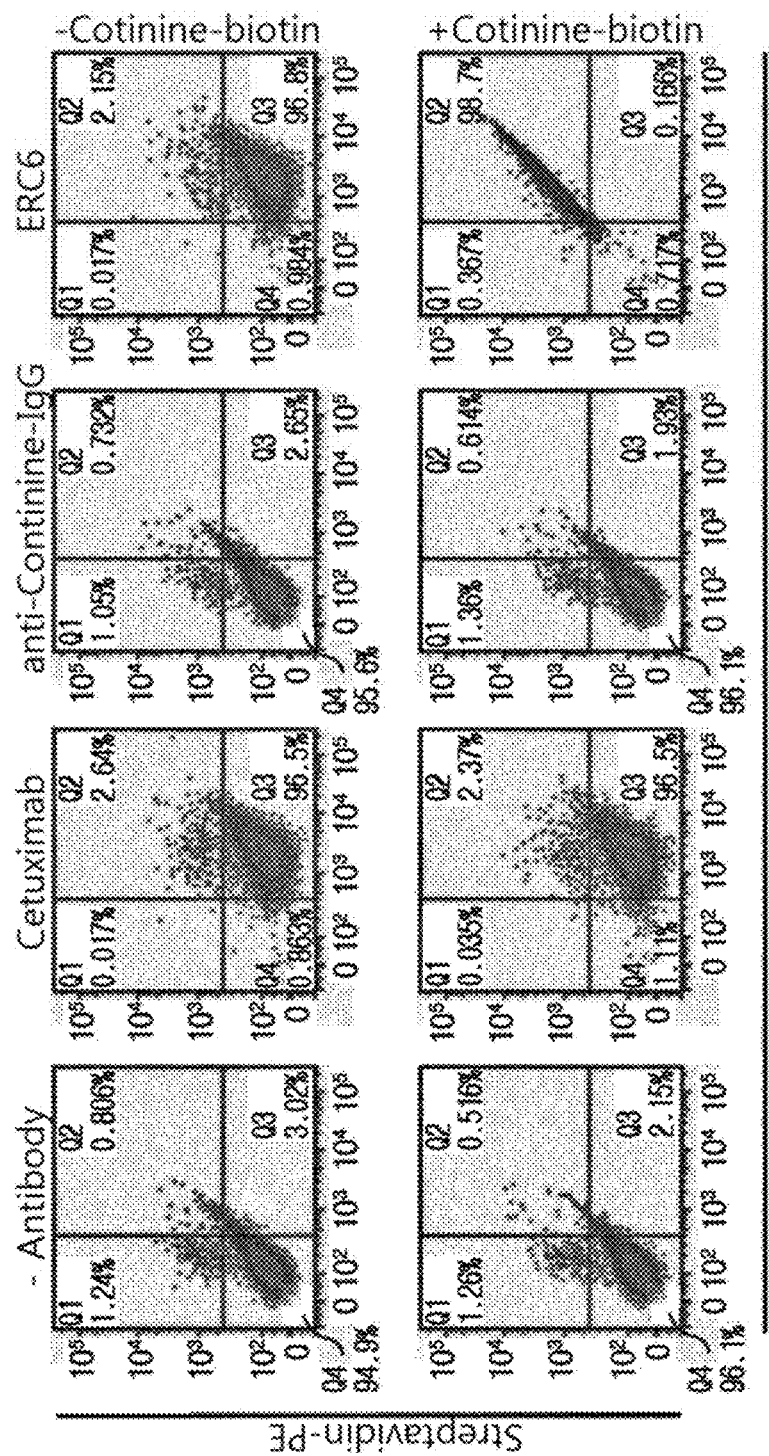
FIGS. 3a, 3b, 3c, 3d and 3e show the enhanced antiproliferative effect of the ERC6-complexed cotinine-duocarmycin in the EGFR positive lung adenocarcinoma cell line.
Figure 3B:
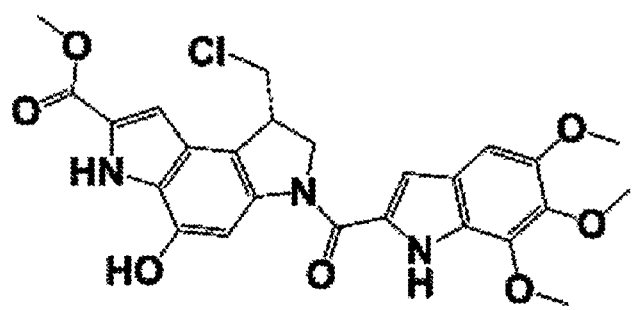
Figure 3C:
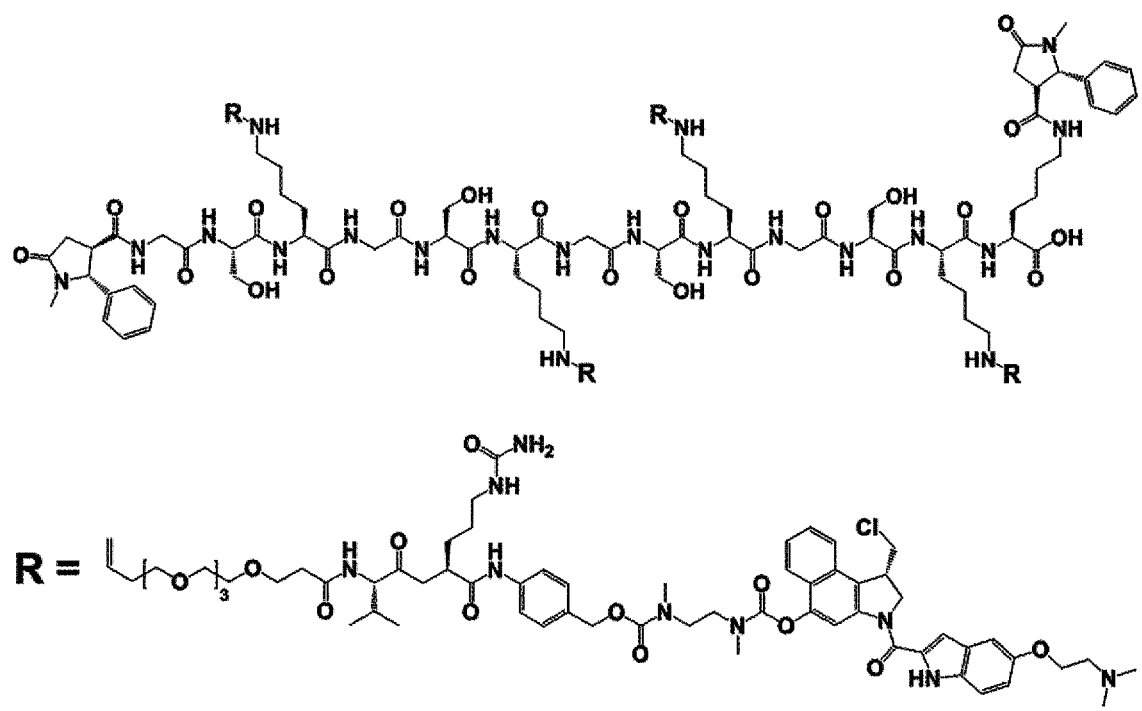

Before the cytotoxicity analysis, the expression of EGFR on the A549 cell surface was confirmed by flow cytometry analysis (FIG. 3a). The ERC6 showed the binding activity similar to the EGFR expressed in the plasma membrane in the similar level to cetuximab. As predicted, the cotinine-biotin showed the binding activity to the A549 cell, when the ERC6 was present. The mixture of the cotinine-biotin and anti-cotinine IgG or cetuximab did not produce any significant signal derived from streptavidin-PE. Additionally, the cotinine-biotin did not affect the binding capacity of ERC6 to EGFR. These data demonstrated that the ERC6 mediated the delivery of cotinine-biotin to EGFR positive cells in the target specific manner by simultaneous binding activity.

Figure 3D:
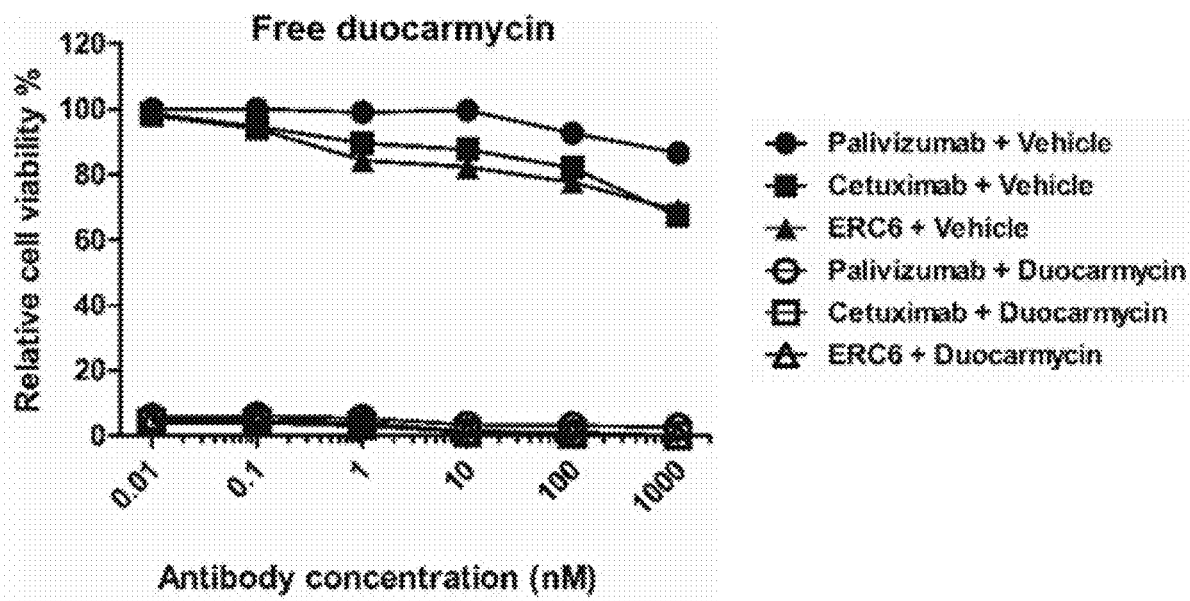
Figure 3E:
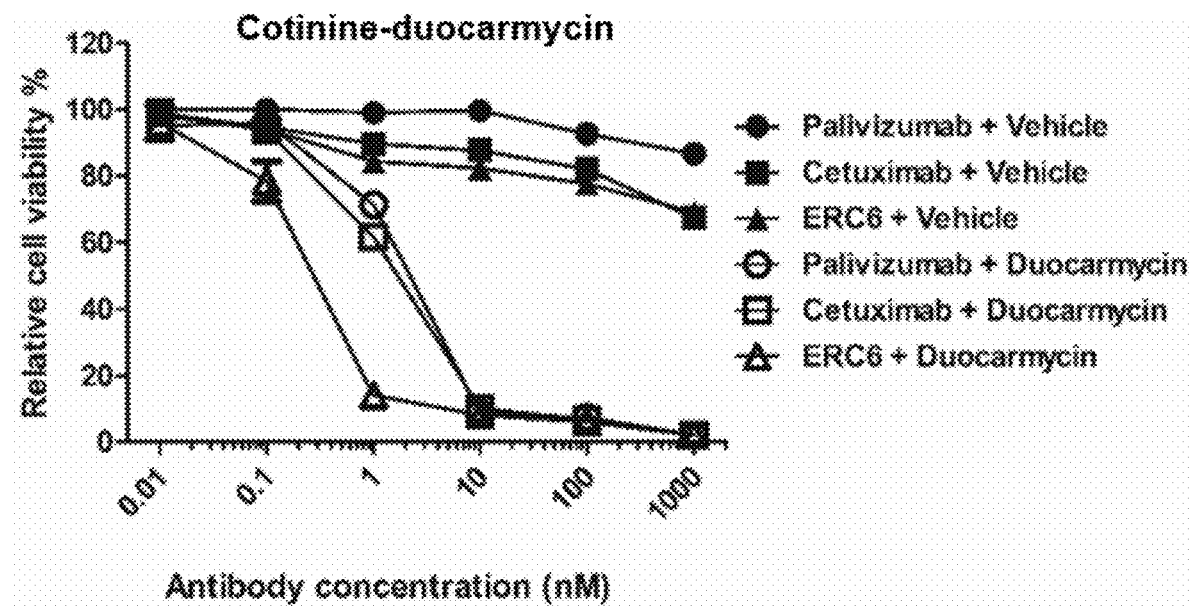

The cytotoxic activity to the A549 cell was investigated by cell viability analysis FIG. 3e). The relative cell viability was determined by measuring the cell ATP content directly related to the number of survivable cells. Duocarmycin without payloads (free duocarmycin) showed the stronger anti-tumor effect than the cotinine-duocarmycin (FIG. 3d, 3e). If the toxicity of cotinine-duocarmycin is lower than free duocarmycin, the penetration via the cytoplasmic membrane may be less effective.

The ERC6 or cetuximab also could not significantly inhibit the proliferation of the A549 cell, due to the primary resistance to the EGFR targeted treatment of the A549 cell (FIG. 3e). However, when the ERC6 and cotinine-duocarmycin were combined, the cytotoxic effect was significantly enhanced than the cotinine-duocarmycin mixture, compared to cetuximab or antibody of negative control.

The half of the maximum inhibitory concentration ($IC_{50}$) was 0.3 nM. The experimental result demonstrated that the ERC6 effectively facilitated internalization of cotinine-duocarmycin with the EGFR positive cell, through receptor-mediated endocytosis. As a result, KRAS-mediated primary resistance of the ERC6-complexed cotinine-duocarmycin was overcome.

Figure 6B:
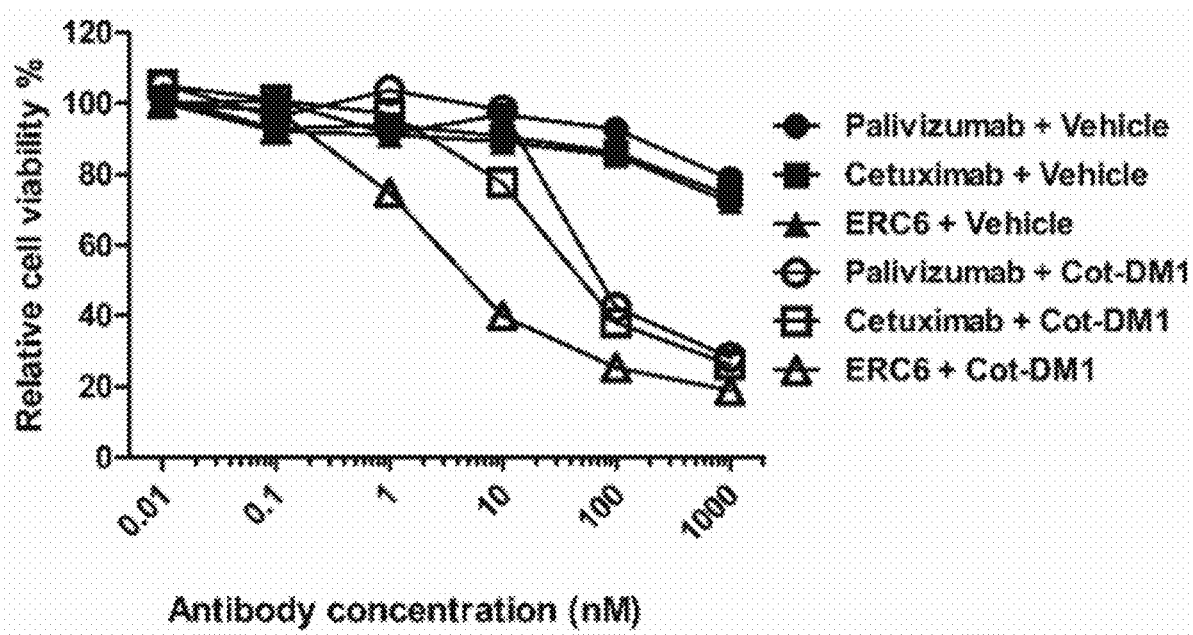
FIG. 6b is the cell viability analysis result of cotinine-DM1 (emtansine). The A549 cell line was treated with palivizumab and DMSO (●); cetuximab and DMSO (■); ERC6 and DMSO (▲); palivizumab and cotinine-DM1 (○); cetuximab and cotinine-DM1 (□); ERC6 and cotinine-DM1 (Δ). Palivizumab was used as the isotype control of bispecific antibody. DMSO was used as the vehicle control of cotinine-duocarmycin. After culturing cells for 72 hrs, the cell ATP content was measured using Cell Titer-Glo reagent, thereby measuring the relative cell viability. The result was shown as mean±SD obtained from the experiments performed three times.

In addition, through additional experiments, the cytotoxic effect of the antibody drug conjugate, in which the ERC6 and cotinine-emtansine (Cot-DM1) were combined, was experimented. This antibody drug conjugate also showed the significantly high cytotoxic effect to the A549 cell line, as same as the cotinine-duocarmycin-combined conjugate (FIG. 6b).

Experimental Example 5: ERC6-Complexed Cotinine-Duocarmycin Inhibiting Tumor Growth in Animal Model Having Lung Adenocarcinoma To evaluate the in vivo efficacy of ERC6-complexed cotinine-duocarmycin, cetuximab-refractory A549 cells were grafted to mice (n=4/group). When the tumor volume reached 150 mm³, mice were intraperitoneally injected with palivizumab and cotinine-duocarmycin, ERC6 and vehicle or ERC6-complexed duocarmycin for five weeks. Drugs were administered to the mice twice a week for two weeks, and then thrice a week for three weeks.

Figure 4A:
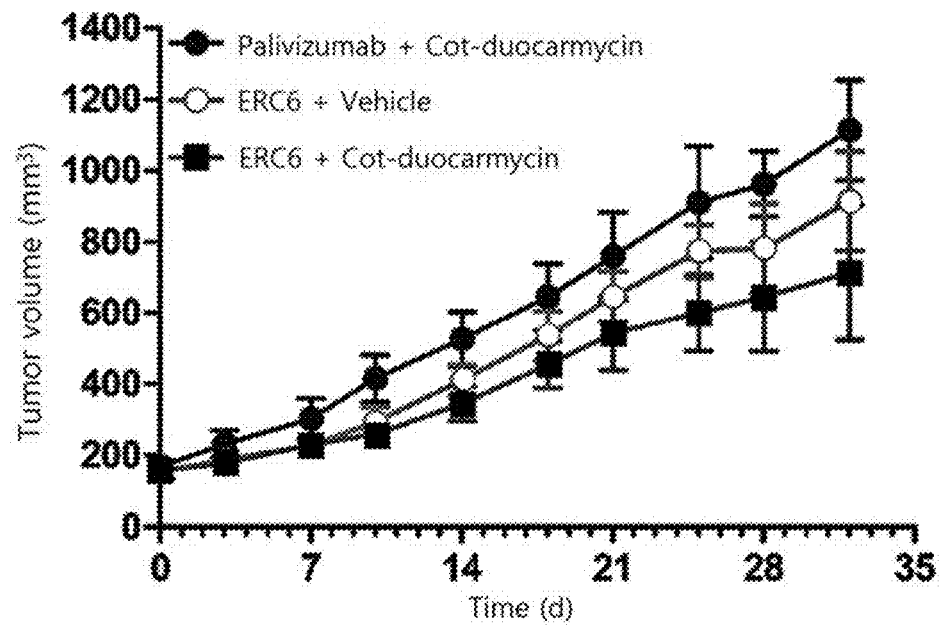
FIGS. 4a, 4b, 4c, 4d and 4e show the enhance antiproliferative effect of the ERC6-complexed cotinine duocarmycin in the mouse xenograft tumor model. A549 cells were subcutaneously injected to the left and right flanks of each Balb/c-nude mouse. When the tumor volume reached 150 mm³, mice were divided to three groups randomly (n=4/group) and treated for 5 weeks. Each group was intraperitoneally injected with palivizumab and cotinine-duocarmycin, ERC6 and vehicle or ERC6-complexed cotinine-duocarmycin. Palivizumab was used as the isotype control of bispecific antibody. DMSO was used as the vehicle control of cotinine duocarmycin.

The mice receiving ERC6-complexed cotinine-duocarmycin showed inhibition of tumor growth, in comparison with animals treated with cotinine-duocarmycin or ERC6 alone (FIG. 4a). Although cotinine-duocarmycin showed potent anti-proliferative effect on A549 in vitro, the isotype control of bispecific antibody did not inhibit the tumor growth in vivo. This observation result showed that only the cotinine-duocarmycin could not be selectively delivered to the tumor site and inhibit the tumor growth. The rapid removal from the mouse bloodstream due to non-specificity and low molecular weight can explain this efficacy insufficiency. On the other hand, the ERC6 allowed the cotinine-duocarmycin to extend the circulating half-life and be delivered to EGFR expressing tumor tissues. Thus, the ERC6 and cotinine-duocarmycin synergistically increase the anti-proliferative efficacy in EGFR-positive cetuximab-refractory tumor in vivo.

Figure 4B:
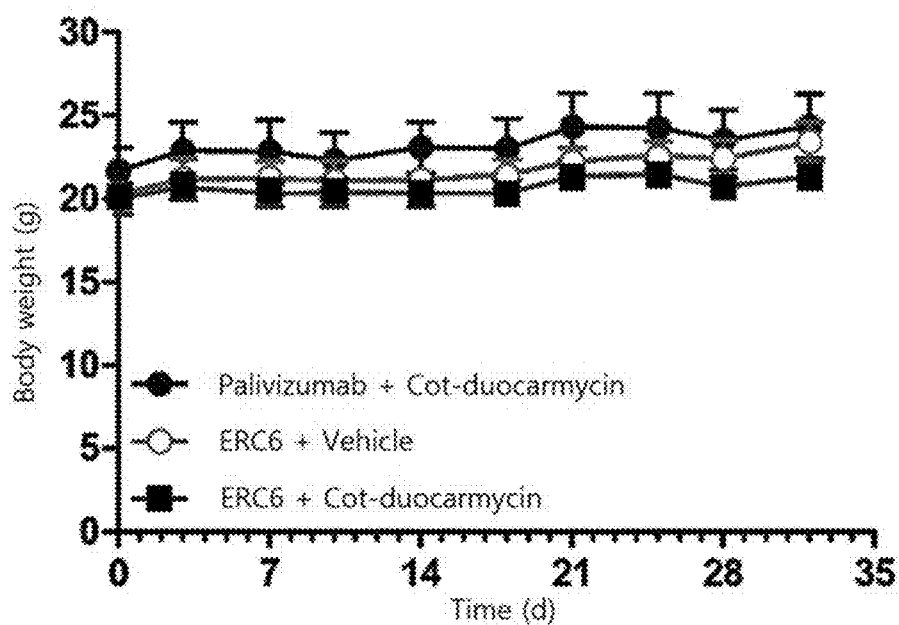
Figure 4C:
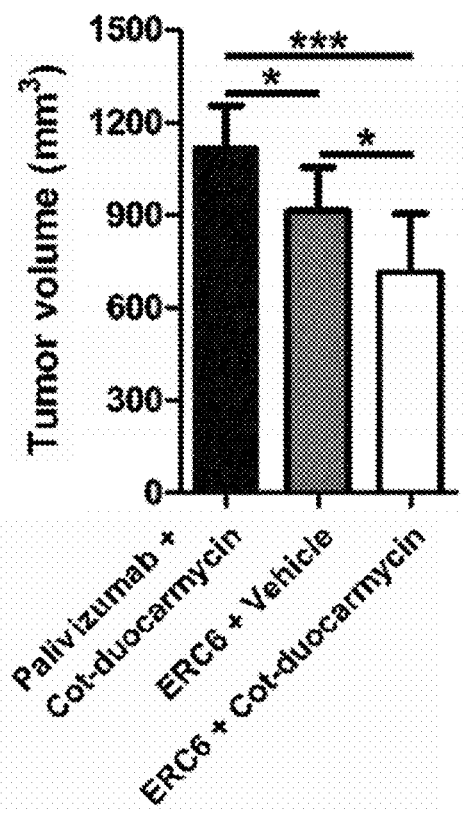
Figure 4D:
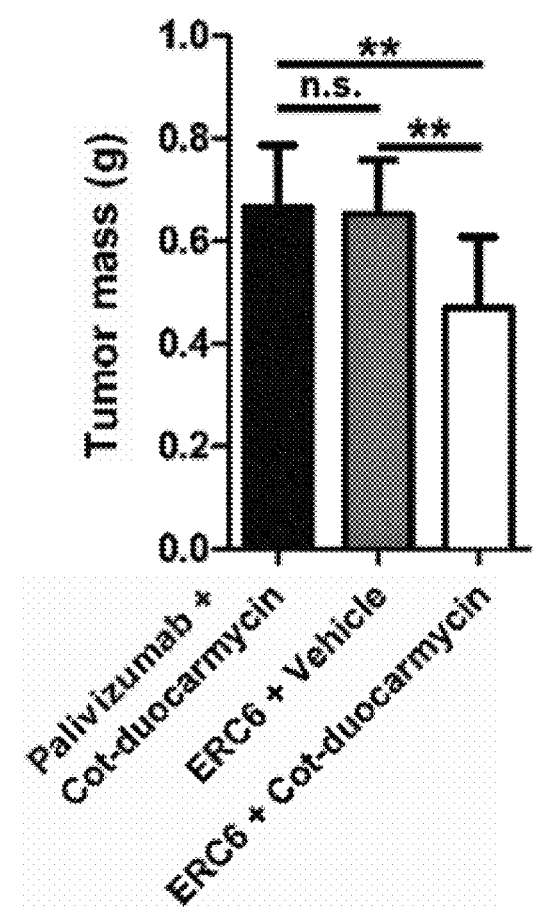
Figure 4E:
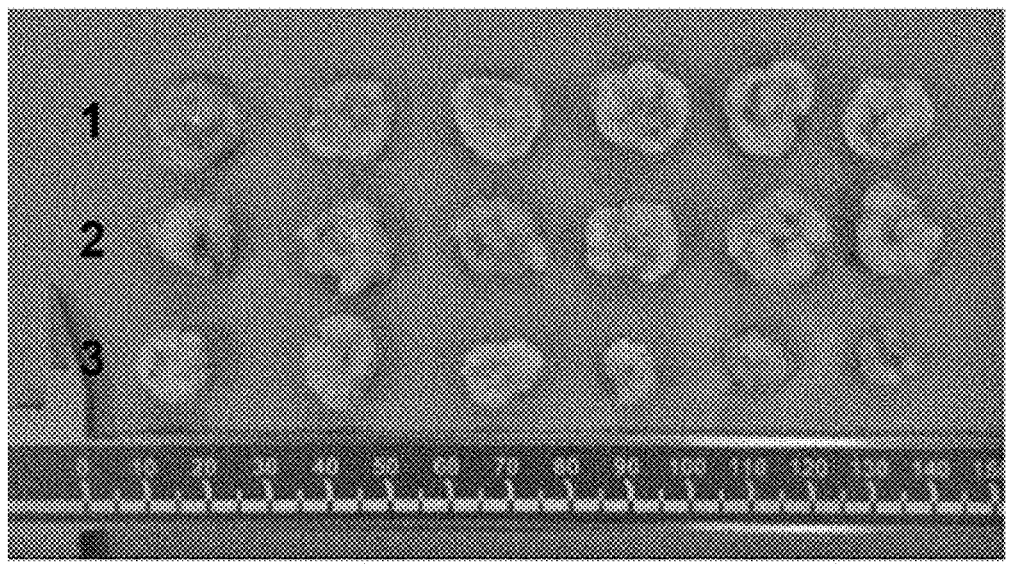

In addition, there was no significant body weight decrease in mice during the treatment period of 5 weeks (FIG. 4b). This observation result indirectly means that the ERC6 and cotinine-duocarmycin did not have systemic toxicity. Consequentially, these data indicate that the ERC6 can function as a drug delivery system and selectively deliver a cotinine-binding cytotoxic drug to EGFR expressing tumor tissues in the target specific manner without systemic toxicity.

Experimental Example 6: Tissue Distribution of ERC6-Complexed Cotinine Payloads in Mouse Xenograft Tumor Model The pharmacokinetics demonstrated that the circulating half-life of the ERC6-complexed payloads was extended by binding to ERC6. To investigate the specific delivery of cotinine payloads into antigen expressing tumor tissues, immunofluorescence analysis was performed in the A549 xenograft mouse model. The A549 cell was subcutaneously injected to the left flank of each Balb/c-nude mouse. When the tumor reached 500 mm$^3$, palivizumab and cotinine-biotin, cetuximab and vehicle or ERC6-complexed cotinine-biotin was intraperitoneally injected to mice having tumor. In 24 hrs after injection, animals were sacrificed, and dissected tumor tissues were imaged ex vivo. Cotinine payloads and antibodies on tumor tissues were detected through fluorescence-labeled secondary antibody. The antibody was detected by Alexa 594-labeled anti-human Fc (red), and the cotinine-biotin was detected by Alexa 488-labeled streptavidin (green). For reference, nuclei were stained by DAPI (blue), and the image magnification was x40. The tissue distribution of ERC6-complexed cotinine-biotin was observed through a confocal microscope.

Compared to palivizumab used as the isotype control of bispecific antibody, the accumulation of ERC6 was observed in the human EGFR positive tumor tissue. In addition, the position of the cotinine-biotin in tumor was observed only in case of injecting ERC6. The cotinine-biotin without ERC6 can be removed rapidly in blood stream due to its low molecular weight. This observation result demonstrates that the ERC6 selectively delivers cotinine payloads to the desired tumor site in the target specific manner in vivo.

---

What is claimed is:

1. An antibody drug conjugate comprising:
a bispecific antibody comprising an anti-cotinine single chain variable fragment (scFv); and
a conjugate of bivalent cotinine which is cross-linked with a peptide, and a drug,
wherein the anti-cotinine single chain variable fragment (scFv) consists of a heavy chain of SEQ ID NO: 2 and a light chain of SEQ ID NO: 4,
wherein the peptide which is cross-linked with bivalent cotinine is 6-18 mer peptide consisting of one or more selected from the consisting of glycine (G), serine (S) and lysine (K).

2. The antibody drug conjugate according to the claim 1, wherein the bivalent cotinine is that two cotinines are cross-linked to the N terminal and C-terminal of a 6-18 mer peptide, respectively.

3. The antibody drug conjugate according to the claim 1, wherein the drug is conjugated with a lysine residue in the 6-18 mer peptide cross-linked with the bivalent cotinine.

4. The antibody drug conjugate according to the claim 1, wherein the bispecific antibody is that a peptide linker $(Gly\text{-}Gly\text{-}Gly\text{-}Gly\text{-}Ser)_3$ is inserted between $C_H3$ domain in heavy-chain constant region of the bispecific antibody and the anti-cotinine single chain variable fragment (scFv).

5. The antibody drug conjugate according to the claim 1, wherein the drug is any one selected from the group consisting of duocarmycin, auristatin, colchicine, anthracycline, calicheamicin, maytansinoid, pyrrolobenzodiazepine, dolastatin, tubulysin, maytansinoid, doxorubicin, cryptophycin, epothilone, safranin, deacetyl colchicine, maytansinol, vedotin, mafodotin, emtansine, mertansine, ravtansine, soravtansine, talirine, tesirine, indolinobenzodiazepines, irinotecan prodrug, exatecan derivative and tubulin inhibitor; or siRNA inhibiting expression of a gene occurring cancer.

6. The antibody drug conjugate according to the claim 1, wherein the bispecific antibody comprises any one selected from the group consisting of cetuximab, trastuzumab, oregovomab, edrecolomab, alemtuzumab, labetuzumab, bevacizumab, ibritumomab, ofatumumab, panitumumab, rituximab, tositumomab, ipilimumab, gemtuzumab, brentuximab, vadastuximab, glembatumumab, depatuxizumab, polatuzumab, denintuzumab, enfortumab, telisotuzumab, tisotumab, pinatuzumab, lifastuzumab, indusatumab, vandortuzumab, sofituzumab, vorsetuzumab, trastuzumab, mirvetuximab, coltuximab, naratuximab, indatuximab, anetumab, lorvotuzumab, cantuzumab, laprituximab, bivatuzumab, vadastuximab, rovalpituzumab, inotuzumab, sacituzumab, labetuzumab, milatuzumab, lupartumab and aprutumab.

7. A pharmaceutical composition for treating cancer comprising the antibody drug conjugate of claim 1.

8. The pharmaceutical composition for treating cancer according to claim 7, wherein the cancer is lung adenocarcinoma having KRAS mutation.

9. A method for treating cancer in a patient comprising a step of administering a therapeutically effective dose of the antibody drug conjugate of claim 1 to the patient.

10. A method for enhancing a half-life of a drug in a patient comprising a step of administering a therapeutically effective dose of the antibody drug conjugate of claim 1 to the patient.

11. A method for preparing an antibody drug conjugate comprising:
   (s1) a step of preparing a bispecific antibody comprising an anti-cotinine single chain variable fragment (scFv);
   (s2) a step of preparing a conjugate of a bivalent cotinine which is cross-linked with a peptide and a drug; and
   (s3) a step of mixing the bispecific antibody produced in the (s1) step and the conjugate produced in the (s2) step.

12. The method for preparing an antibody drug conjugate according to claim 11, wherein the bivalent cotinine is that two cotinines are cross-linked to the N terminal and C-terminal of a 6-18 mer peptide, respectively.

13. The method for preparing an antibody drug conjugate according to claim 11, wherein the drug is conjugated with a lysine residue in the 6-18 mer peptide cross-linked with the bivalent cotinine.

\* \* \* \* \*

SEQUENCE LISTING

```
<160> NUMBER OF SEQ ID NOS: 18

<210> SEQ ID NO 1
<211> LENGTH: 357
<212> TYPE: DNA
<213> ORGANISM: Artificial Sequence
<220> FEATURE:
<223> OTHER INFORMATION: heavy chain of anti-cotinine scFv

<400> SEQUENCE: 1
gaggtgcagc tggtggagag cgggggcggc ctggtgcagc ctggaggaag cctgcgactg      60
tcctgtgcag cttctggaca cctgcggaga agggactgga tgaactgggt gcggcaggca     120
ccaggaaaag gcctggagtg ggtcgcagcc atcggacgat ccggcgacac ctactatgct     180
acatgggcaa aaggcaggtt cacaattagt gctgatactt caaagaacac cgcatacctg     240
cagatgaata gtctgagggc cgaagacact gctgtgtact attgctcccg catcccttat     300
tttgggtgga acaatggaga tatttggggg cagggaacac tggtgactgt cagctcc       357

<210> SEQ ID NO 2
<211> LENGTH: 119
<212> TYPE: PRT
<213> ORGANISM: Artificial Sequence
<220> FEATURE:
<223> OTHER INFORMATION: heavy chain of anti-cotinine scFv

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly His Leu Arg Arg Arg Asp
            20                  25                  30

Trp Met Asn Trp Val Arg Gln Ala Pro Gly Lys Gly Leu Glu Trp Val
        35                  40                  45

Ala Ala Ile Gly Arg Ser Gly Asp Thr Tyr Tyr Ala Thr Trp Ala Lys
    50                  55                  60
```

```
Gly Arg Phe Thr Ile Ser Ala Asp Thr Ser Lys Asn Thr Ala Tyr Leu
 65                  70                  75                  80

Gly Met Asn Ser Leu Arg Ala Glu Asp Thr Ala Val Tyr Tyr Cys Ser
                 85                  90                  95

Arg Ile Pro Tyr Phe Gly Trp Asn Asn Gly Asp Ile Trp Gly Gln Gly
            100                 105                 110

Thr Leu Val Thr Val Ser Ser
            115

<210> SEQ ID NO 3
<211> LENGTH: 330
<212> TYPE: DNA
<213> ORGANISM: Artificial Sequence
<220> FEATURE:
<223> OTHER INFORMATION: light chain of anti-cotinine scFv

<400> SEQUENCE: 3
gacatccaga tgacacagtc tccatctagt ctgagtgcat cagtgggcga tagagtcacc      60
attacatgtc agtcaagcca gagtccctac tcaaacgagt ggctgagctg gtatcagcag    120
aagcccggaa agcccctaa gctgctgatc tacaggatta gcacactggc ttccggcgtg     180
ccttctcggt tcagcggctc cagatctggg actgacttta ctctgaccat ctcctctctg    240
cagccagagg atttcgcaac ctactattgc gccggcgggt ataattttgg cctgttcctg    300
tttggccagg ggaccaaagt ggaaattaag                                     330

<210> SEQ ID NO 4
<211> LENGTH: 110
<212> TYPE: PRT
<213> ORGANISM: Artificial Sequence
<220> FEATURE:
<223> OTHER INFORMATION: light chain of anti-cotinine scFv

<400> SEQUENCE: 4

Asp Ile Gln Met Thr Gln Ser Pro Ser Ser Leu Ser Ala Ser Val Gly
  1               5                  10                  15

Asp Arg Val Thr Ile Thr Cys Gln Ser Ser Gln Ser Pro Tyr Ser Asn
                 20                  25                  30

Glu Trp Leu Ser Trp Tyr Gln Gln Lys Pro Gly Lys Ala Pro Lys Leu
            35                  40                  45

Leu Ile Tyr Arg Ile Ser Thr Leu Ala Ser Gly Val Pro Ser Arg Phe
     50                  55                  60

Ser Gly Ser Arg Ser Gly Thr Asp Phe Thr Leu Thr Ile Ser Ser Leu
 65                  70                  75                  80

Gln Pro Glu Asp Phe Ala Thr Tyr Tyr Cys Ala Gly Gly Tyr Asn Phe
                 85                  90                  95

Gly Leu Phe Leu Phe Gly Gln Gly Thr Lys Val Glu Ile Lys
            100                 105                 110

<210> SEQ ID NO 5
<211> LENGTH: 1347
<212> TYPE: DNA
<213> ORGANISM: Artificial Sequence
<220> FEATURE:
<223> OTHER INFORMATION: heavy chain of cetuximab

<400> SEQUENCE: 5
caggtgcagc tgaagcagag cggccccgga ctggtgcagc cctcacagag cctgtccatc      60
acttgcaccg tgagtggctt ctcactgaca aactacggag tccactgggt gcgacagagc    120
```

```
cctggcaagg ggctggagtg gctgggcgtg atctggtccg agggaacac tgactataat    180
actcccttca ccagccggct gtccattaac aaggataact ctaagagtca ggtgttcttt    240
aagatgaact ctctgcagag taatgacaca gctatctact attgcgctcg cgcactgact    300
tactatgatt acgagttcgc atattgggga cagggcacac tggtcaccgt gagcgccgcc    360
agcaccaagg gacccagcgt gtttccactg cccccagct ccaaatcaac cagcggagga     420
acagcagccc tgggatgtct ggtgaaggac tacttcccag aacccgtcac agtgtcctgg    480
aactctgggg cactgacatc tggagtccat acttttccag ccgtgctgca gtctagtggg    540
ctgtacagcc tgtcaagcgt ggtcactgtc ccctcctcta gtctgggaac acagacttat    600
atctgcaacg tgaatcacaa gccaagtaat accaaggtcg acaaagagt ggagcccaag     660
agctgtgata aaacccatac atgccccct tgtcctgcac agaactgct ggggggaccc      720
tccgtgttcc tgtttccacc caagcctaaa gacacctga tgatttctag gactcccgag    780
gtcacctgcg tggtcgtgga cgtgagccac gaggatcctg aagtcaagtt caactggtac    840
gtggatggcg tcgaagtgca taatgctaag acaaaacctc gggaggaaca gtacaacagc    900
acttatagag tcgtgtccgt cctgaccgtg ctgcaccagg attggctgaa cgggaaagag    960
tataagtgca aagtgagcaa taaggccctg cccgctccta tcgagaaaac catttccaag    1020
gccaaaggcc agcctaggga accacaggtg tacacactgc ctccatcccg cgaggaaatg    1080
accaagaacc aggtctctct gacatgtctg gtgaaaggat tctatccttc agacatcgct    1140
gtggagtggg aaagcaatgg ccagccagag aacaattaca gaccacacc ccctgtgctg     1200
gacagtgatg gctcattctt tctgtattct aagctgaccg tggataaaag tcgatggcag    1260
cagggggaatg tcttttcctg ttctgtgatg cacgaagccc tgcacaacca ttacacccag    1320
aagagcctga gcctgtcccc cggcaaa                                         1347

<210> SEQ ID NO 6
<211> LENGTH: 449
<212> TYPE: PRT
<213> ORGANISM: Artificial Sequence
<220> FEATURE:
<223> OTHER INFORMATION: heavy chain of cetuximab

<400> SEQUENCE: 6

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 7
<211> LENGTH: 642
<212> TYPE: DNA
<213> ORGANISM: Artificial Sequence
<220> FEATURE:
<223> OTHER INFORMATION: light chain of cetuximab

<400> SEQUENCE: 7
gatattctgc tgactcagag ccccgtgatt ctgtctgtca gccccggcga gcgggtgtct      60
ttcagttgca gagcatcaca gagcatcgga acaaatattc actggtacca gcagaggact     120
aacggctccc cacgcctgct gatcaagtat gcttccgaat ctatcagtgg gattccctct     180
cggttctcag gcagcgggtc cggaacagac tttactctgt ctatcaatag tgtggagtca     240
gaagacattg ccgattacta ttgccagcag aacaataact ggcctaccac attcggcgct     300
```

```
gggaccaagc tggagctgaa acgaacagtg gcctgctccaa gtgtcttcat ttttccccct    360
agcgacgaac agctgaaatc cgggaccgcc tctgtggtct gtctgctgaa taacttttac    420
cctagagagg caaaggtgca gtggaaagtc gataatgccc tgcagagcgg aaactcccag    480
gagtctgtga ctgaacagga cagtaaggat tcaacctata gcctgagctc cactctgacc    540
ctgtccaaag ctgattacga aaagcataaa gtctatgcat gtgaggtcac tcatcagggg    600
ctgtccagtc cagtcaccaa gtccttcaat cggggggaat gc                       642
```

<210> SEQ ID NO 8
<211> LENGTH: 214
<212> TYPE: PRT
<213> ORGANISM: Artificial Sequence
<220> FEATURE:
<223> OTHER INFORMATION: light chain of cetuximab

<400> SEQUENCE: 8

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 9
<211> LENGTH: 214
<212> TYPE: PRT
<213> ORGANISM: Artificial Sequence
<220> FEATURE:
<223> OTHER INFORMATION: light chain of tetravalent complex comprising
      bispecific cetuximab x anti-cotinine antibody

<400> SEQUENCE: 9

```
Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30
```

```
                  20                  25                  30

Ile His Trp Tyr Gln Gln Arg Thr Asn Gly Ser Pro Arg Leu Leu Ile
             35                  40                  45

Lys Tyr Ala Ser Glu Ser Ile Ser Gly Ile Pro Ser Arg Phe Ser Gly
         50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 715
<212> TYPE: PRT
<213> ORGANISM: Artificial Sequence
<220> FEATURE:
<223> OTHER INFORMATION: heavy chain of tetravalent complex comprising
      bispecific cetuximab x anti-cotinine antibody

<400> SEQUENCE: 10

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
         35                  40                  45

Gly Val Ile Trp Ser Gly Gly Asn Thr Asp Tyr Asn Thr Pro Phe Thr
     50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
        180                 185                 190
Ser Ser Leu Gly Thr Gln Thr Tyr Ile Cys Asn Val Asn His Lys Pro
    195                 200                 205
Ser Asn Thr Lys Val Asp Lys Arg Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys Thr Ser Gly Gly Gly Ser Gly Gly Gly Ser Gly Gly Gly
    450                 455                 460
Gly Ser Glu Val Gln Leu Val Glu Ser Gly Gly Gly Leu Val Gln Pro
465                 470                 475                 480
Gly Gly Ser Leu Arg Leu Ser Cys Ala Ala Ser Gly His Leu Arg Arg
            485                 490                 495
Arg Asp Trp Met Asn Trp Val Arg Gln Ala Pro Gly Lys Gly Leu Glu
            500                 505                 510
Trp Val Ala Ala Ile Gly Arg Ser Gly Asp Thr Tyr Tyr Ala Thr Trp
        515                 520                 525
Ala Lys Gly Arg Phe Thr Ile Ser Ala Asp Thr Ser Lys Asn Thr Ala
    530                 535                 540
Tyr Leu Gln Met Asn Ser Leu Arg Ala Glu Asp Thr Ala Val Tyr Tyr
545                 550                 555                 560
Cys Ser Arg Ile Pro Tyr Phe Gly Trp Asn Asn Gly Asp Ile Trp Gly
            565                 570                 575
Gln Gly Thr Leu Val Thr Val Ser Ser Gly Gly Gly Gly Ser Gly Gly
```

```
                    580                 585                 590
Gly Ser Gly Gly Gly Gly Ser Gly Gly Gly Ser Asp Ile Gln
        595                 600                 605
Met Thr Gln Ser Pro Ser Ser Leu Ser Ala Ser Val Gly Asp Arg Val
    610                 615                 620
Thr Ile Thr Cys Gln Ser Ser Gln Ser Pro Tyr Ser Asn Glu Trp Leu
625                 630                 635                 640
Ser Trp Tyr Gln Gln Lys Pro Gly Lys Ala Pro Lys Leu Leu Ile Tyr
                645                 650                 655
Arg Ile Ser Thr Leu Ala Ser Gly Val Pro Ser Arg Phe Ser Gly Ser
            660                 665                 670
Arg Ser Gly Thr Asp Phe Thr Leu Thr Ile Ser Ser Leu Gln Pro Glu
        675                 680                 685
Asp Phe Ala Thr Tyr Tyr Cys Ala Gly Gly Tyr Asn Phe Gly Leu Phe
    690                 695                 700
Leu Phe Gly Gln Gly Thr Lys Val Glu Ile Lys
705                 710                 715

<210> SEQ ID NO 11
<211> LENGTH: 5
<212> TYPE: PRT
<213> ORGANISM: Artificial Sequence
<220> FEATURE:
<223> OTHER INFORMATION: generic linker sequence that can be repeated 1
      to 5 times

<400> SEQUENCE: 11

Gly Gly Gly Gly Ser
1               5

<210> SEQ ID NO 12
<211> LENGTH: 20
<212> TYPE: PRT
<213> ORGANISM: Artificial Sequence
<220> FEATURE:
<223> OTHER INFORMATION: Linker

<400> SEQUENCE: 12

Gly Gly Gly Gly Ser Gly Gly Gly Gly Ser Gly Gly Gly Gly Ser Gly
1               5                   10                  15

Gly Gly Gly Ser
            20

<210> SEQ ID NO 13
<211> LENGTH: 15
<212> TYPE: PRT
<213> ORGANISM: Artificial Sequence
<220> FEATURE:
<223> OTHER INFORMATION: Linker

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 6
<212> TYPE: PRT
<213> ORGANISM: Artificial Sequence
<220> FEATURE:
<223> OTHER INFORMATION: Linke

<400> SEQUENCE: 14
```

```
<210> SEQ ID NO 15
<211> LENGTH: 12
<212> TYPE: PRT
<213> ORGANISM: Artificial Sequence
<220> FEATURE:
<223> OTHER INFORMATION: Linker

<400> SEQUENCE: 15

Gly Gly Gly Gly Ser Lys Gly Gly Gly Ser Lys
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Linker

<400> SEQUENCE: 16

Gly Ser Lys Gly Ser Lys Gly Ser Lys Gly Ser Lys Lys
1               5                   10

<210> SEQ ID NO 17
<211> LENGTH: 18
<212> TYPE: PRT
<213> ORGANISM: Artificial Sequence
<220> FEATURE:
<223> OTHER INFORMATION: Linker

<400> SEQUENCE: 17

Gly Gly Gly Ser Gly Gly Gly Ser Lys Gly Gly Gly Ser Gly Gly Gly
1               5                   10                  15

Ser Lys

<210> SEQ ID NO 18
<211> LENGTH: 13
<212> TYPE: PRT
<213> ORGANISM: Artificial Sequence
<220> FEATURE:
<223> OTHER INFORMATION: Linker

<400> SEQUENCE: 18

Gly Ser Lys Gly Ser Lys Gly Ser Lys Gly Ser Lys Lys
1               5                   10
```